United States Patent
Yoon et al.

(10) Patent No.: US 7,301,015 B2
(45) Date of Patent: Nov. 27, 2007

(54) GENOTYPING KIT FOR DIAGNOSIS OF HUMAN PAPILLOMA VIRUS INFECTION

(75) Inventors: Sung-Wook Yoon, Seoul (KR); Tae-Shin Park, Seoul (KR); Jeong-Mi Kim, Seoul (KR); Mi-Sun Park, Busan (KR)

(73) Assignee: Biomedlab Corporation, Seoul (KR)

( * ) Notice: Subject to any disclaimer, the term of this patent is extended or adjusted under 35 U.S.C. 154(b) by 160 days.

(21) Appl. No.: 10/489,550

(22) PCT Filed: Sep. 18, 2001

(86) PCT No.: PCT/KR01/01562

§ 371 (c)(1),
(2), (4) Date: Aug. 9, 2004

(87) PCT Pub. No.: WO03/027323

PCT Pub. Date: Apr. 3, 2003

(65) Prior Publication Data

US 2004/0265794 A1    Dec. 30, 2004

(30) Foreign Application Priority Data

Sep. 14, 2001 (KR) .................. 10-2001-0056827

(51) Int. Cl.
*C07H 21/04* (2006.01)
*C07H 21/02* (2006.01)

(52) U.S. Cl. .................. 536/23.1; 536/24.3; 435/287.2

(58) Field of Classification Search .................. None
See application file for complete search history.

(56) References Cited

U.S. PATENT DOCUMENTS 5,447,839 A * 9/1995 Manos et al. .................. 435/5
5,484,699 A * 1/1996 Bouma et al. .................. 435/5
5,861,242 A   1/1999 Chee et al. .................... 435/5

FOREIGN PATENT DOCUMENTS

WO    WO 95/22626    8/1995
WO    WO 99/14377    3/1999

OTHER PUBLICATIONS

"The Use of the Polymerase Chain Reaction for the Detection of Human Papillomavirus Type 13", Williamson et al., Journal of Virological Methods, 31 1991, pp. 57-66.
"Human Papillomavirus Type 13 Coat Protein Gene (L1), Partial cds", Database EMBL Online, Jan. 24, 1992, 2 pages.
"Human Papilloma Virus Type 13 DNA", Database EMBL Online, Oct. 23, 1992, 5 pages.
"Genotyping of 27 Human Papillomavirus Types by Using L1 Consensus PCR Products by a Single-Hybridization, Reverse Line Blot Detection Method", Gravitt et al., Journal of Clinical Microbiology, vol. 36, No. 10, Oct. 1998, pp. 3020-3027.
"Genotyping of the Human Papillomavirus in Condyloma Acuminata", Jifeng Liu, et al, Chin J Derm Venereol, Jan. 2001.

* cited by examiner

*Primary Examiner*—Diana Johannsen
*Assistant Examiner*—Amanda Shaw
(74) *Attorney, Agent, or Firm*—Marshall, Gerstein & Borun LLP

(57) ABSTRACT

The present invention relates to a genotyping kit for diagnosis of detecting the human papillomavirus (HPV) infection, probes for genotyping the HPV, and DNA chips including the probes. Also, the present invention relates to a method for diagnosis of HPV infection.

5 Claims, 33 Drawing Sheets

SEQUENCE LISTING

<160> NUMBER OF SEQ ID NOS: 54

<210> SEQ ID NO 1
<211> LENGTH: 30

<212> TYPE: DNA
<213> ORGANISM: Artificial Sequence
<220> FEATURE:
<223> OTHER INFORMATION: porbe HPV 13

<400> SEQUENCE: 1
acatcatctc tttcagacac atataaggcc                                   30

<210> SEQ ID NO 2
<211> LENGTH: 30
<212> TYPE: DNA
<213> ORGANISM: Artificial Sequence
<220> FEATURE:
<223> OTHER INFORMATION: probe HPV 26

<400> SEQUENCE: 2
agtacattat ctgcagcatc tgcatccact                                   30

<210> SEQ ID NO 3
<211> LENGTH: 30
<212> TYPE: DNA
<213> ORGANISM: Artificial Sequence
<220> FEATURE:
<223> OTHER INFORMATION: probe HPV 30

<400> SEQUENCE: 3
ttatccacat ataattcaag ccaaattaaa                                   30

<210> SEQ ID NO 4
<211> LENGTH: 30
<212> TYPE: DNA
<213> ORGANISM: Artificial Sequence
<220> FEATURE:
<223> OTHER INFORMATION: probe HPV 43

<400> SEQUENCE: 4
cctctactga ccctactgtg cccagtacat                                   30

<210> SEQ ID NO 5
<211> LENGTH: 32
<212> TYPE: DNA
<213> ORGANISM: Artificial Sequence
<220> FEATURE:
<223> OTHER INFORMATION: porbe HPV 53

<400> SEQUENCE: 5
tctacatata attcaaagca aattaaacag ta                                32

<210> SEQ ID NO 6
<211> LENGTH: 31
<212> TYPE: DNA
<213> ORGANISM: Artificial Sequence
<220> FEATURE:
<223> OTHER INFORMATION: probe HPV 54

<400> SEQUENCE: 6
tacagcatcc acgcaggata gctttaataa t                                 31

<210> SEQ ID NO 7
<211> LENGTH: 30
<212> TYPE: DNA
<213> ORGANISM: Artificial Sequence
<220> FEATURE:
<223> OTHER INFORMATION: probe HPV 54

<400> SEQUENCE: 7
catccacgca ggatagcttt aataattctg     30

<210> SEQ ID NO 8
<211> LENGTH: 33
<212> TYPE: DNA
<213> ORGANISM: Artificial Sequence
<220> FEATURE:
<223> OTHER INFORMATION: probe HPV 55

<400> SEQUENCE: 8
tgtgctgcta caactcagtc tccatctaca aca     33

<210> SEQ ID NO 9
<211> LENGTH: 33
<212> TYPE: DNA
<213> ORGANISM: Artificial Sequence
<220> FEATURE:
<223> OTHER INFORMATION: probe HPV 57

<400> SEQUENCE: 9
gaaactaatt ataaagcctc caattataag gaa     33

<210> SEQ ID NO 10
<211> LENGTH: 31
<212> TYPE: DNA
<213> ORGANISM: Artificial Sequence
<220> FEATURE:
<223> OTHER INFORMATION: probe HPV 61

<400> SEQUENCE: 10
ctgtatctga atataaagcc acaagcttta g     31

<210> SEQ ID NO 11
<211> LENGTH: 30
<212> TYPE: DNA
<213> ORGANISM: Artificial Sequence
<220> FEATURE:
<223> OTHER INFORMATION: probe HPV 61

<400> SEQUENCE: 11
cctgtatctg aatataaagc cacaagcttt     30

<210> SEQ ID NO 12
<211> LENGTH: 30
<212> TYPE: DNA
<213> ORGANISM: Artificial Sequence
<220> FEATURE:
<223> OTHER INFORMATION: probe HPV 62

<400> SEQUENCE: 12
cctccactgc tgcagcagaa tacacggcta     30

<210> SEQ ID NO 13
<211> LENGTH: 33
<212> TYPE: DNA
<213> ORGANISM: Artificial Sequence
<220> FEATURE:
<223> OTHER INFORMATION: probe HPV 64

<400> SEQUENCE: 13
tacaaatcca ccatatgcaa acactaattt taa     33

<210> SEQ ID NO 14
<211> LENGTH: 30
<212> TYPE: DNA
<213> ORGANISM: Artificial Sequence

```
<220> FEATURE:
<223> OTHER INFORMATION: probe HPV 67

<400> SEQUENCE: 14
tatgttctga ggaaaaatca gaggctacat                                           30

<210> SEQ ID NO 15
<211> LENGTH: 33
<212> TYPE: DNA
<213> ORGANISM: Artificial Sequence
<220> FEATURE:
<223> OTHER INFORMATION: probe HPV 68

<400> SEQUENCE: 15
tttgtctact actactgaat cagctgtacc aaa                                       33

<210> SEQ ID NO 16
<211> LENGTH: 33
<212> TYPE: DNA
<213> ORGANISM: Artificial Sequence
<220> FEATURE:
<223> OTHER INFORMATION: probe HPV 69

<400> SEQUENCE: 16
aatctgcatc tgccactttt aaaccatcag att                                       33

<210> SEQ ID NO 17
<211> LENGTH: 30
<212> TYPE: DNA
<213> ORGANISM: Artificial Sequence
<220> FEATURE:
<223> OTHER INFORMATION: probe HPV 70

<400> SEQUENCE: 17
aacggccata cctgctgtat atagccctac                                           30

<210> SEQ ID NO 18
<211> LENGTH: 30
<212> TYPE: DNA
<213> ORGANISM: Artificial Sequence
<220> FEATURE:
<223> OTHER INFORMATION: probe HPV 70

<400> SEQUENCE: 18
accgaaacgg ccatacctgc tgtatatagc                                           30

<210> SEQ ID NO 19
<211> LENGTH: 30
<212> TYPE: DNA
<213> ORGANISM: Artificial Sequence
<220> FEATURE:
<223> OTHER INFORMATION: probe HPV 74

<400> SEQUENCE: 19
cgccttctgc tacatataat agttcagact                                           30

<210> SEQ ID NO 20
<211> LENGTH: 30
<212> TYPE: DNA
<213> ORGANISM: Artificial Sequence
<220> FEATURE:
<223> OTHER INFORMATION: probe HPV JC9710

<400> SEQUENCE: 20
aaacaccctc tgacacatac aaggcttcca                                           30
```

```
<210> SEQ ID NO 21
<211> LENGTH: 30
<212> TYPE: DNA
<213> ORGANISM: Artificial Sequence
<220> FEATURE:
<223> OTHER INFORMATION: probe HPV 16

<400> SEQUENCE: 21
gtgctgccat atctacttca gaaactacat                                    30

<210> SEQ ID NO 22
<211> LENGTH: 34
<212> TYPE: DNA
<213> ORGANISM: Artificial Sequence
<220> FEATURE:
<223> OTHER INFORMATION: probe HPV 16

<400> SEQUENCE: 22
tatgtgctgc catatctact tcagaaacta cata                               34

<210> SEQ ID NO 23
<211> LENGTH: 30
<212> TYPE: DNA
<213> ORGANISM: Artificial Sequence
<220> FEATURE:
<223> OTHER INFORMATION: probe HPV 34

<400> SEQUENCE: 23
ggtacacaat ccacaagtac aactgcacca                                    30

<210> SEQ ID NO 24
<211> LENGTH: 30
<212> TYPE: DNA
<213> ORGANISM: Artificial Sequence
<220> FEATURE:
<223> OTHER INFORMATION: probe HPV 35

<400> SEQUENCE: 24
ttctgctgtg tcttctagtg acagtacata                                    30

<210> SEQ ID NO 25
<211> LENGTH: 36
<212> TYPE: DNA
<213> ORGANISM: Artificial Sequence
<220> FEATURE:
<223> OTHER INFORMATION: probe HPV 35

<400> SEQUENCE: 25
gcacggtctg tgtgttctgc tgtgtcttct acgtgc                             36

<210> SEQ ID NO 26
<211> LENGTH: 30
<212> TYPE: DNA
<213> ORGANISM: Artificial Sequence
<220> FEATURE:
<223> OTHER INFORMATION: probe HPV 40

<400> SEQUENCE: 26
cttatgtgct gccacacagt cccccacacc                                    30

<210> SEQ ID NO 27
<211> LENGTH: 30
<212> TYPE: DNA
<213> ORGANISM: Artificial Sequence
<220> FEATURE:
<223> OTHER INFORMATION: probe HPV 56
```

```
<400> SEQUENCE: 27
tattagtact gctacagaac agttaagtaa                                    30

<210> SEQ ID NO 28
<211> LENGTH: 30
<212> TYPE: DNA
<213> ORGANISM: Artificial Sequence
<220> FEATURE:
<223> OTHER INFORMATION: probe HPV 58

<400> SEQUENCE: 28
cactgaagta actaaggaag gtacatataa                                    30

<210> SEQ ID NO 29
<211> LENGTH: 30
<212> TYPE: DNA
<213> ORGANISM: Artificial Sequence
<220> FEATURE:
<223> OTHER INFORMATION: probe HPV 59

<400> SEQUENCE: 29
tctactactt cttctattcc taatgtatac                                    30

<210> SEQ ID NO 30
<211> LENGTH: 30
<212> TYPE: DNA
<213> ORGANISM: Artificial Sequence
<220> FEATURE:
<223> OTHER INFORMATION: probe HPV 66

<400> SEQUENCE: 30
ctaaaagcac attaactaaa tatgatgccc                                    30

<210> SEQ ID NO 31
<211> LENGTH: 30
<212> TYPE: DNA
<213> ORGANISM: Artificial Sequence
<220> FEATURE:
<223> OTHER INFORMATION: probe HPV 6

<400> SEQUENCE: 31
atccgtaact acatcttcca catacaccaa                                    30

<210> SEQ ID NO 32
<211> LENGTH: 30
<212> TYPE: DNA
<213> ORGANISM: Artificial Sequence
<220> FEATURE:
<223> OTHER INFORMATION: probe HPV 11

<400> SEQUENCE: 32
atctgtgtct aaatctgcta catacactaa                                    30

<210> SEQ ID NO 33
<211> LENGTH: 30
<212> TYPE: DNA
<213> ORGANISM: Artificial Sequence
<220> FEATURE:
<223> OTHER INFORMATION: probe HPV 18

<400> SEQUENCE: 33
tgcttctaca cagtctcctg tacctgggca                                    30

<210> SEQ ID NO 34
```

```
<211> LENGTH: 30
<212> TYPE: DNA
<213> ORGANISM: Artificial Sequence
<220> FEATURE:
<223> OTHER INFORMATION: probe HPV 31

<400> SEQUENCE: 34
tgtttgtgct gcaattgcaa acagtgatac                                              30

<210> SEQ ID NO 35
<211> LENGTH: 30
<212> TYPE: DNA
<213> ORGANISM: Artificial Sequence
<220> FEATURE:
<223> OTHER INFORMATION: probe HPV 33

<400> SEQUENCE: 35
tttatgcaca caagtaacta gtgacagtac                                              30

<210> SEQ ID NO 36
<211> LENGTH: 30
<212> TYPE: DNA
<213> ORGANISM: Artificial Sequence
<220> FEATURE:
<223> OTHER INFORMATION: probe HPV 39

<400> SEQUENCE: 36
tctacctcta tagagtcttc cataccttct                                              30

<210> SEQ ID NO 37
<211> LENGTH: 30
<212> TYPE: DNA
<213> ORGANISM: Artificial Sequence
<220> FEATURE:
<223> OTHER INFORMATION: probe HPV 42

<400> SEQUENCE: 37
ctgcaacatc tggtgataca tatacagctg                                              30

<210> SEQ ID NO 38
<211> LENGTH: 30
<212> TYPE: DNA
<213> ORGANISM: Artificial Sequence
<220> FEATURE:
<223> OTHER INFORMATION: probe HPV 44

<400> SEQUENCE: 38
gccactacac agtcccctcc gtctacatat                                              30

<210> SEQ ID NO 39
<211> LENGTH: 30
<212> TYPE: DNA
<213> ORGANISM: Artificial Sequence
<220> FEATURE:
<223> OTHER INFORMATION: probe HPV 45

<400> SEQUENCE: 39
acacaaaatc ctgtgccaag tacatatgac                                              30

<210> SEQ ID NO 40
<211> LENGTH: 30
<212> TYPE: DNA
<213> ORGANISM: Artificial Sequence
<220> FEATURE:
<223> OTHER INFORMATION: probe HPV 51

<400> SEQUENCE: 40
```
agcactgcca ctgctgcggt ttccccaaca                              30

<210> SEQ ID NO 41
<211> LENGTH: 30
<212> TYPE: DNA
<213> ORGANISM: Artificial Sequence
<220> FEATURE:
<223> OTHER INFORMATION: probe HPV 52

<400> SEQUENCE: 41
tgctgaggtt aaaaaggaaa gcacatataa                              30

<210> SEQ ID NO 42
<211> LENGTH: 30
<212> TYPE: DNA
<213> ORGANISM: Artificial Sequence
<220> FEATURE:
<223> OTHER INFORMATION: b-globin

<400> SEQUENCE: 42
tgcacctgac tcctgaggag aagtctgccg                              30

<210> SEQ ID NO 43
<211> LENGTH: 23
<212> TYPE: DNA
<213> ORGANISM: Artificial Sequence
<220> FEATURE:
<223> OTHER INFORMATION: primer Gp5+

<400> SEQUENCE: 43
tttkttachg tkgtdgatac yac                                     23

<210> SEQ ID NO 44
<211> LENGTH: 25
<212> TYPE: DNA
<213> ORGANISM: Artificial Sequence
<220> FEATURE:
<223> OTHER INFORMATION: primer Gp6+

<400> SEQUENCE: 44
gaaahataaa ytgyaadtca taytc                                   25

<210> SEQ ID NO 45
<211> LENGTH: 18
<212> TYPE: DNA
<213> ORGANISM: Artificial Sequence
<220> FEATURE:
<223> OTHER INFORMATION: primer BG 1

<400> SEQUENCE: 45
atacaagtca gggcagag                                           18

<210> SEQ ID NO 46
<211> LENGTH: 20
<212> TYPE: DNA
<213> ORGANISM: Artificial Sequence
<220> FEATURE:
<223> OTHER INFORMATION: primer BG 2

<400> SEQUENCE: 46
cttaaacctg tcttgtaacc                                         20

<210> SEQ ID NO 47
<211> LENGTH: 30
<212> TYPE: DNA

```
<213> ORGANISM: Artificial Sequence
<220> FEATURE:
<223> OTHER INFORMATION: probe HPV 16

<400> SEQUENCE: 47
gtcattatgt gctgccatat ctacttcaga                                        30

<210> SEQ ID NO 48
<211> LENGTH: 30
<212> TYPE: DNA
<213> ORGANISM: Artificial Sequence
<220> FEATURE:
<223> OTHER INFORMATION: probe HPV 34

<400> SEQUENCE: 48
tacacaatcc acaagtacaa atgcaccata                                        30

<210> SEQ ID NO 49
<211> LENGTH: 30
<212> TYPE: DNA
<213> ORGANISM: Artificial Sequence
<220> FEATURE:
<223> OTHER INFORMATION: probe HPV 35

<400> SEQUENCE: 49
gtctgtgtgt tctgctgtgt cttctagtga                                        30

<210> SEQ ID NO 50
<211> LENGTH: 30
<212> TYPE: DNA
<213> ORGANISM: Artificial Sequence
<220> FEATURE:
<223> OTHER INFORMATION: probe HPV 40

<400> SEQUENCE: 50
gctgccacac agtcccccac accaacccca                                        30

<210> SEQ ID NO 51
<211> LENGTH: 30
<212> TYPE: DNA
<213> ORGANISM: Artificial Sequence
<220> FEATURE:
<223> OTHER INFORMATION: probe HPV 56

<400> SEQUENCE: 51
gtactgctac agaacagtta agtaaatatg                                        30

<210> SEQ ID NO 52
<211> LENGTH: 30
<212> TYPE: DNA
<213> ORGANISM: Artificial Sequence
<220> FEATURE:
<223> OTHER INFORMATION: probe HPV 58

<400> SEQUENCE: 52
attatgcact gaagtaacta aggaaggtac                                        30

<210> SEQ ID NO 53
<211> LENGTH: 30
<212> TYPE: DNA
<213> ORGANISM: Artificial Sequence
<220> FEATURE:
<223> OTHER INFORMATION: probe HPV 59

<400> SEQUENCE: 53
ctgtgtgtgc ttctactact gcttctattc                                        30
```

```
<210> SEQ ID NO 54
<211> LENGTH: 30
<212> TYPE: DNA
<213> ORGANISM: Artificial Sequence
<220> FEATURE:
<223> OTHER INFORMATION: probe HPV 66

<400> SEQUENCE: 54
ctattaatgc agctaaaagc acattaacta                                      30
```

GENOTYPING KIT FOR DIAGNOSIS OF HUMAN PAPILLOMA VIRUS INFECTION

RELATED APPLICATIONS

This application is the U.S. National Phase under 35 U.S.C. 371 of International Application PCT/KR01/01562, filed Sep. 18, 2001, which claims priority of Republic of Korea 10-2001-0056827, filed Sep. 14, 2001.

BACKGROUND OF THE INVENTION (a) Field of the Invention

The present invention relates to a genotyping kit and method for diagnosis of human papillomavirus (HPV) infection, probes for genotyping the HPV, and DNA chips including the probes. More specifically, the present invention relates to a genotyping kit for detecting human papillomaviruses from clinical samples of infected patients using a DNA chip, a process for preparing the said DNA chip, and a method for diagnosis of HPV infection using the genotyping kit.

(b) Description of the Related Art

Uterine cancer includes cervical cancer, endometrial cancer, uterine sarcoma and the like. For cervical cancer, approximately 450,000 new cases occur worldwide each year, approximately 6,000 of these in Korea. Since the occurrence of cervical cancer (including cervical intraepithelial neoplasia) accounts for 22.1% of total cancer cases in Korean women, the highest incidence with the second highest death rate, the prevention, diagnosis and treatment of cervical cancer are regarded as the most important issues in women's health.

Cervical cancer progresses through a precancerous stage, cervical intraepithelial neoplasia (CIN), known to be mainly caused by human papillomavirus (HPV) infection. Especially, infection by particular types of HPV raises the possibility of developing invasive disease. Over 70 genotypes of HPV have been identified since the recognition of HPV as the main etiological factor for cervical cancer, and through research, certain HPV genotypes have been selectively found in lesions of specific locations or progression stages, which has furthered recognition of the biological diversity of HPV infection. Among the HPV genotypes detected in the anogenital area, over 10 genotypes have been classified as being part of the high-risk group that are associated with an elevated risk for developing cervical cancer. Based on these findings, characterization of the biological differences of HPV infection is considered to be of significant importance to the diagnosis and prevention of cervical cancer.

The test that has been most commonly used for the diagnosis of cervical cancer at its early stage is the Pap smear, which is a cytological test performed as follows: old cells removed from the outermost layer of cells from the surface of the cervix are stained and examined for histopathological characteristics of HPV infection including koilocytosis, perinuclear halo formation in the epithelial cells. However, due to the low diagnostic efficiency (1-15%) of Pap tests together with other limitations, additional methods such as colposcopy are necessary for more dependable diagnoses. Colposcopic screening can detect HPV infection at up to 70%, but it has disadvantages including high cost of the equipment, the need for skilled interpreters, and inability of determining HPV genotypes to distinguish between high-risk and low-risk infection. Therefore, efforts have been continuously made to develop techniques for the detection of HPV and identification of HPV genotypes, to supplement conventional screening methods for cervical cancer and its precursors such as the Pap test.

The methods for detection of HPV and identification of HPV genotypes can be classified into two groups, i.e., direct detection of HPV DNA and detection of amplified HPV DNA. The methods for direct detection of HPV DNA include liquid hybridization (Hybrid Capture kit by Digene Diagnostics, Silver Spring, Md., USA, www.digene.com), Southern blot and dot blot with HPV type-specific probes, filter in situ hybridization (FISH) and the like; and methods for the detection of amplified DNA include type-specific PCR (polymerase chain reaction) and general-primer PCR. In particular, genotype analyses of amplified HPV DNA by general primer sets are commonly performed by employing dot blot hybridization, microtitre plate hybridization, or a line probe assay. Among these methods, liquid hybridization by Hybrid Capture and line probe assay following a general-primer PCR have been considered most suitable for diagnostic purposes. The line probe assay can detect about 20 different HPV genotypes by immobilizing oligonucleotide probes on a nitrocellulose membrane, however it lacks reliability due to low sensitivity and difficulties in data interpretation. Commercialized Hybrid Capture kits can detect HPV DNA in clinical samples without PCR amplification, and they can distinguish between high-risk and low-risk HPV groups. But the fact that Hybrid Capture kits cannot identify the genotypes of infecting HPV limits accurate risk determination since the risk factors amongst high-risk HPVs are not the same, in other words, intermediate-risk types are included in the high-risk group. Moreover, the use of an RNA probe may present low stability of the kit, and the possibility of contamination cannot be excluded.

Under these circumstances, there have been strong reasons for exploring and developing a simple and accurate method and a genotyping kit for detection of HPV infection and identification of the genotype of infecting HPV with high specificity and sensitivity, as well as probes for genotyping the HPV, and DNA chips including the probes. In addition, the genotyping kit, the probes and the DNA chips must have specificity and sensitivity high enough to detect various kinds of HPV so that they can diagnose the HPV infection and identify its genotype with accuracy.

SUMMARY OF THE INVENTION

It is one object of the present invention to provide novel probes having nucleotide sequences complementary to DNA of HPV in order to detect HPV infection and identify the genotype of HPV with high specificity and sensitivity.

It is another object of the invention to provide a DNA chip for detection of HPV infection and identification of the HPV genotype, wherein the DNA chip comprises probes having nucleotide sequences complementary to DNA of HPV.

It is yet another object to provide an HPV genotyping kit comprising a novel DNA chip for detection of HPV infection and identification of the HPV genotype.

It is still another object to provide a method for diagnosis of HPV infection and identification of the HPV genotype using a novel DNA chip for detection of HPV infection and identification of the HPV genotype.

It is a further object to provide a method for amplifying sample DNA by a novel PCR in the diagnosis of HPV infection and the identification of the HPV genotype using a novel DNA chip for detection of HPV infection and identification of the HPV genotype.

BRIEF DESCRIPTION OF THE DRAWINGS

FIGS. 1a and 1b are schematic representations of the types and positions of the probes on the DNA chip according to one embodiment of the present invention.

FIG. 2a is a photograph showing the result of HPV 16 DNA analysis using the DNA chip shown in FIG. 1a.

FIG. 2b is a photograph showing the result of HPV 18 DNA analysis using the DNA chip shown in FIG. 1a.

FIG. 2c is a photograph showing the result of HPV 39 DNA analysis using the DNA chip shown in FIG. 1a.

FIG. 2d is a photograph showing the result of HPV 58 DNA analysis using the DNA chip shown in FIG. 1a.

FIG. 2e is a photograph showing the result of HPV 68 DNA analysis using the DNA chip shown in FIG. 1a.

FIG. 2f is a photograph showing the result of HPV 69 DNA analysis using the DNA chip shown in FIG. 1a.

FIG. 2g is a photograph showing the result of HPV 6 DNA analysis using the DNA chip shown in FIG. 1a.

FIG. 2h is a photograph showing the result of HPV 11 DNA analysis using the DNA chip shown in FIG. 1a.

FIG. 2i is a photograph showing the result of HPV 43 DNA analysis using the DNA chip shown in FIG. 1a.

FIG. 2j is a photograph showing the result of HPV 44 DNA analysis using the DNA chip shown in FIG. 1a.

FIG. 3i is a photograph showing the result of analyzing a sample triple-infected with HPV 16, HPV 52 and HPV 59 using the DNA chip of the present invention.

DETAILED DESCRIPTION OF THE PREFERRED EMBODIMENTS

Figure 2A:
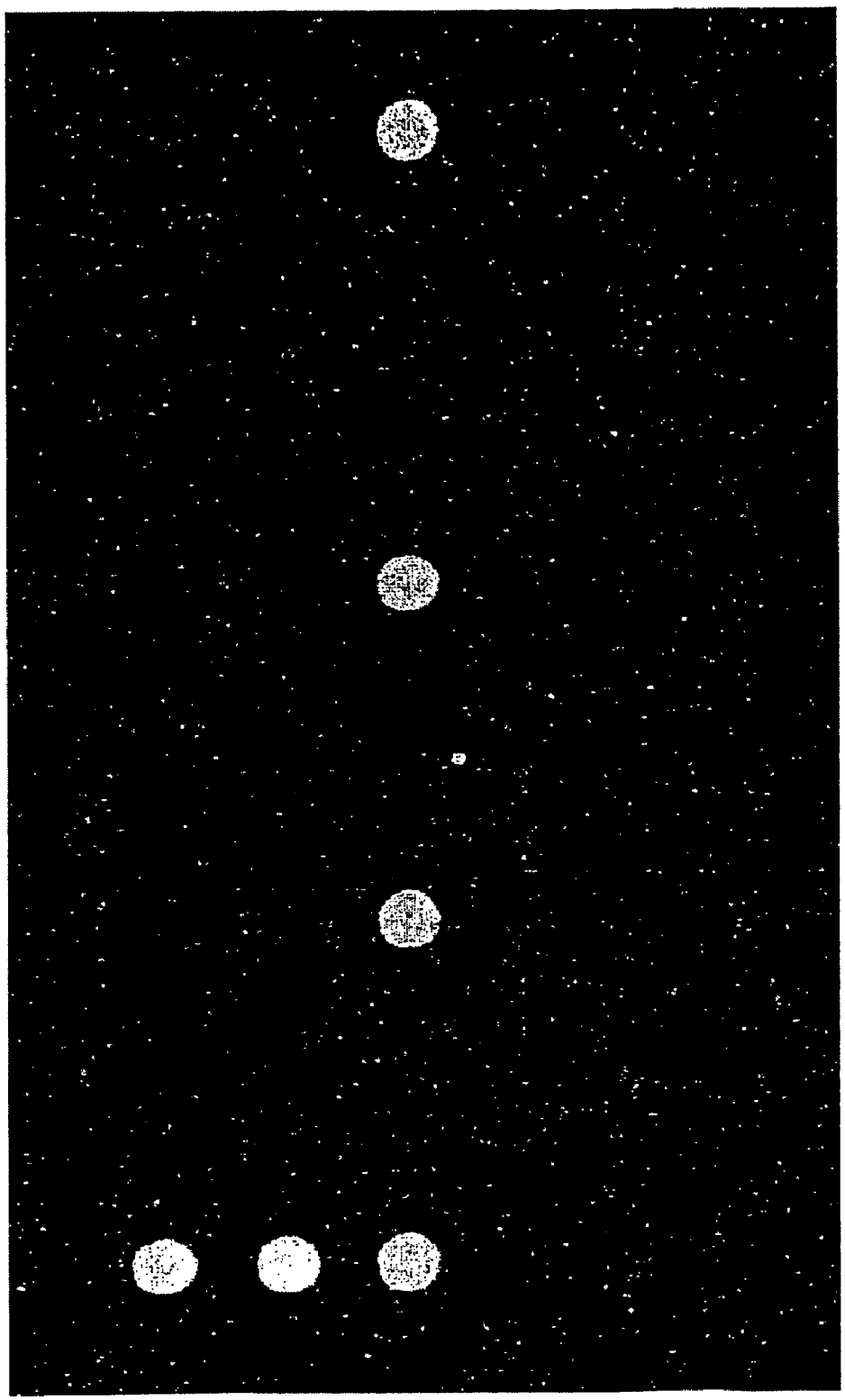
Figure 2B:
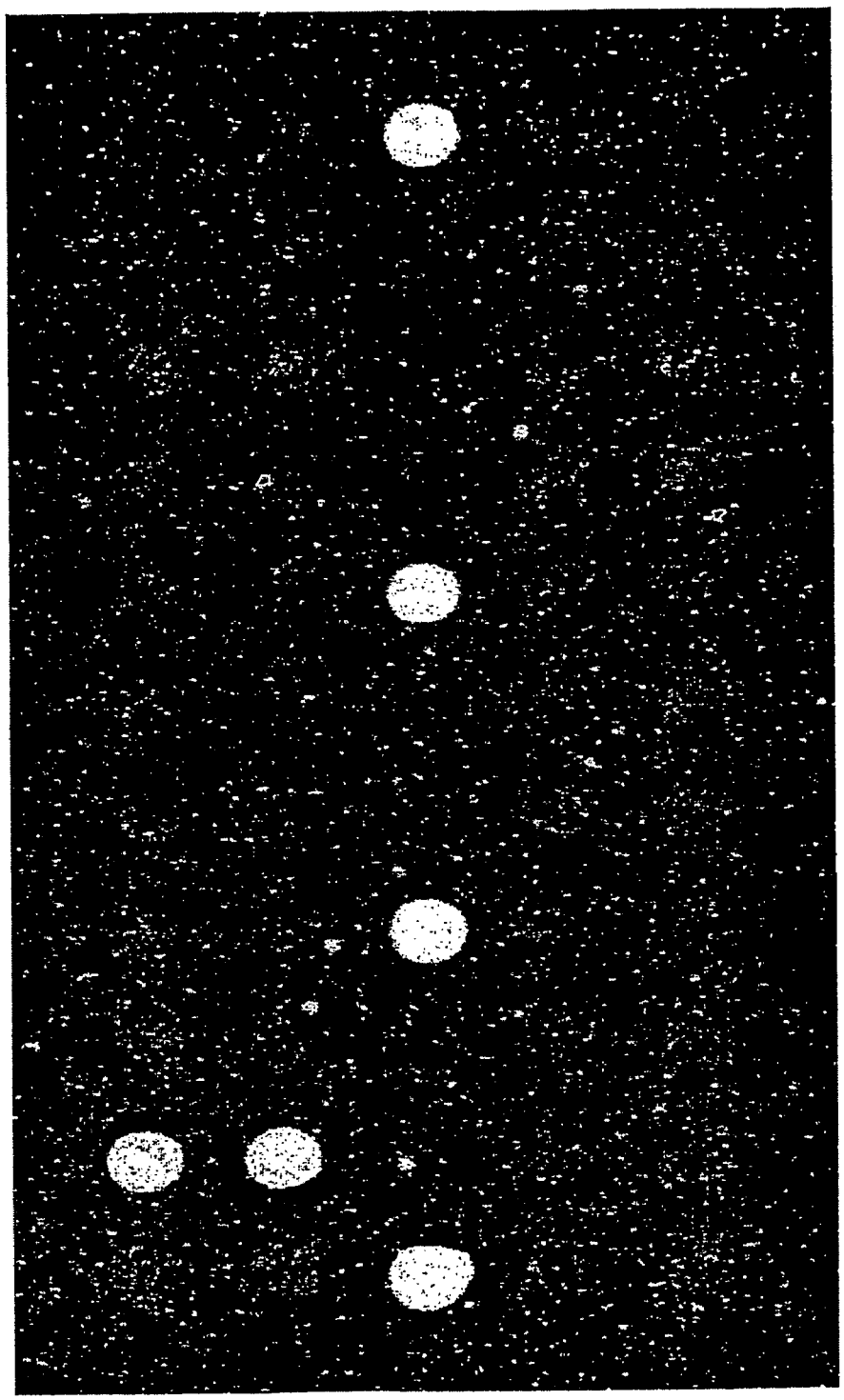
Figure 2C:
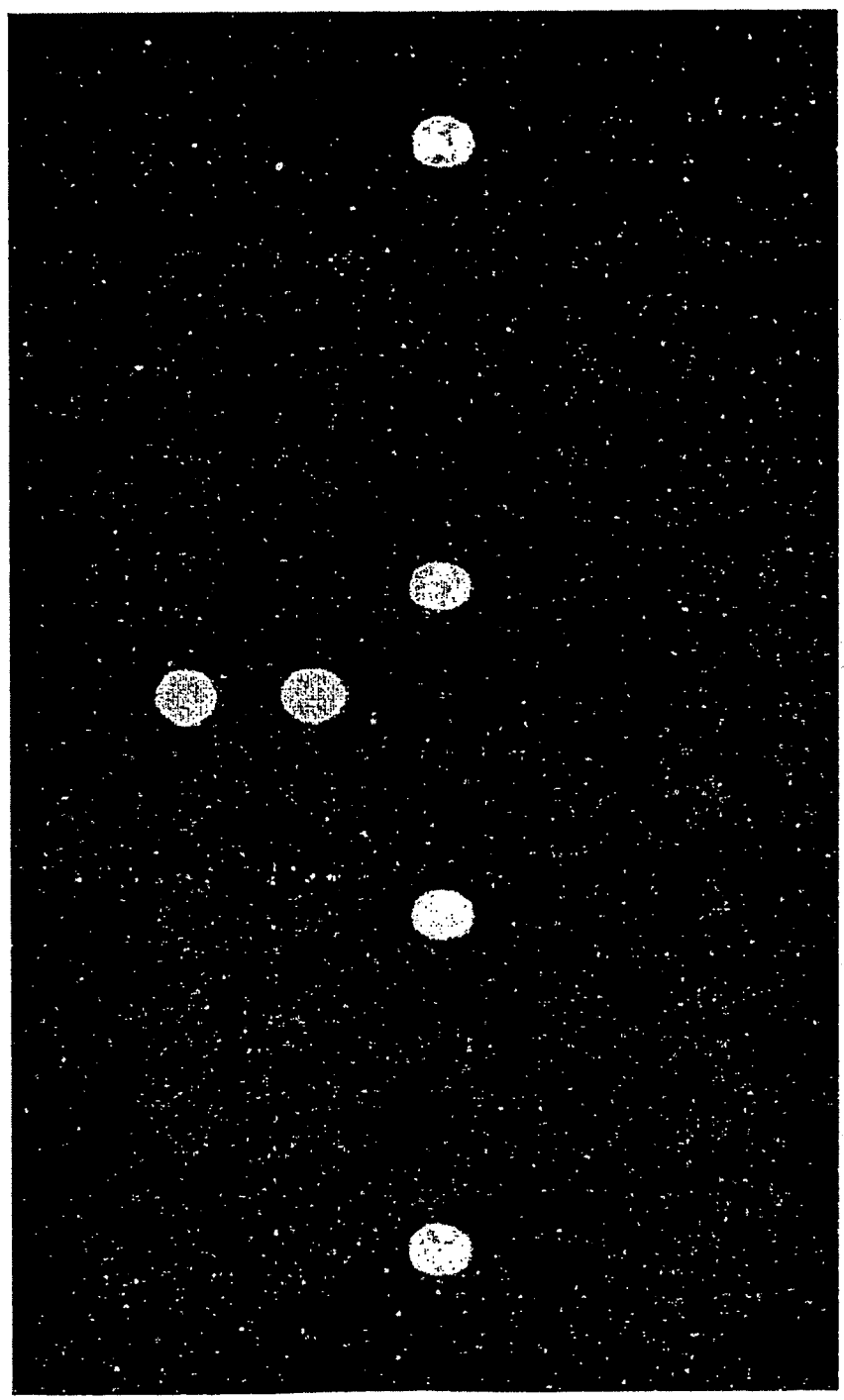
Figure 2D:
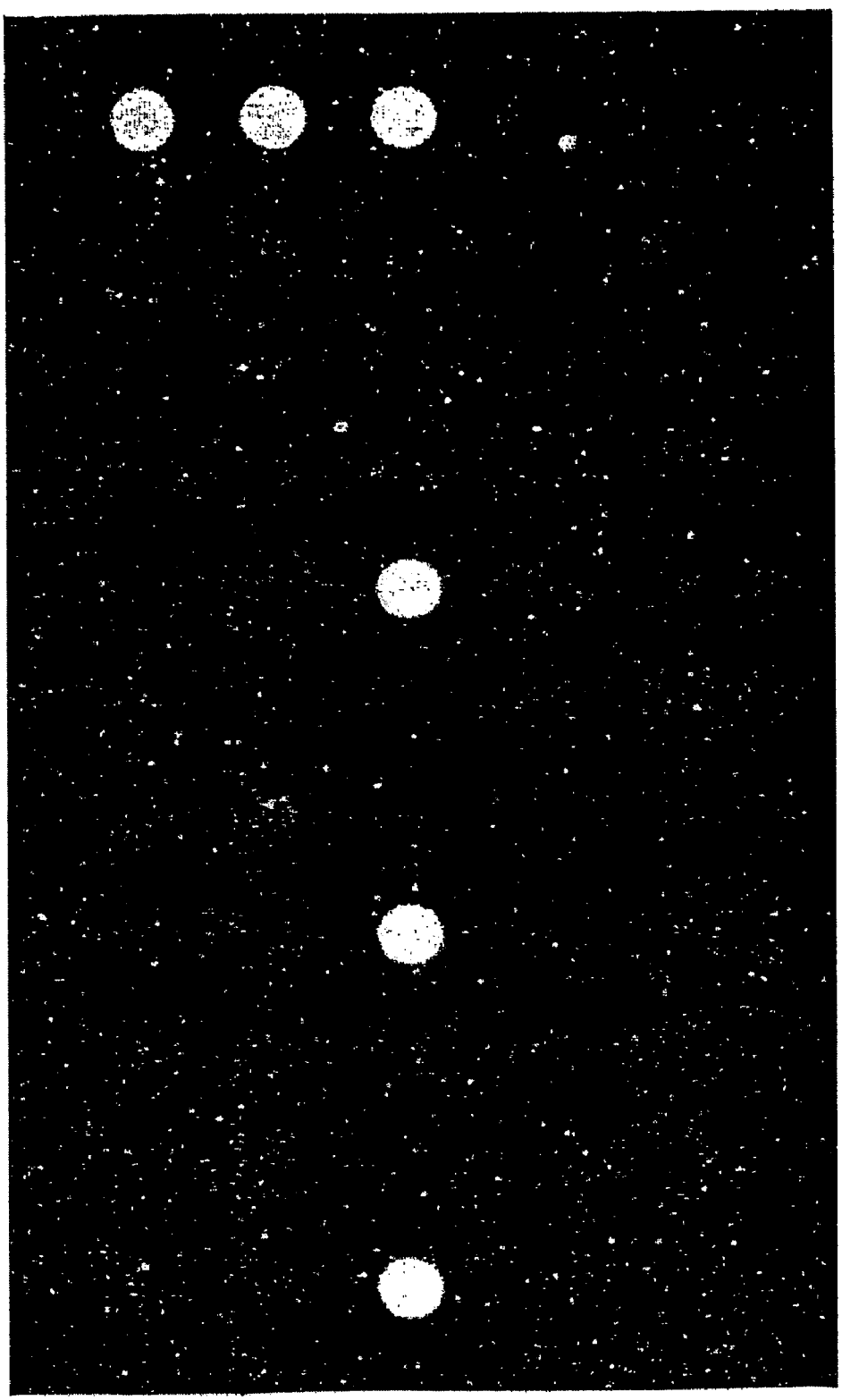
Figure 2E:
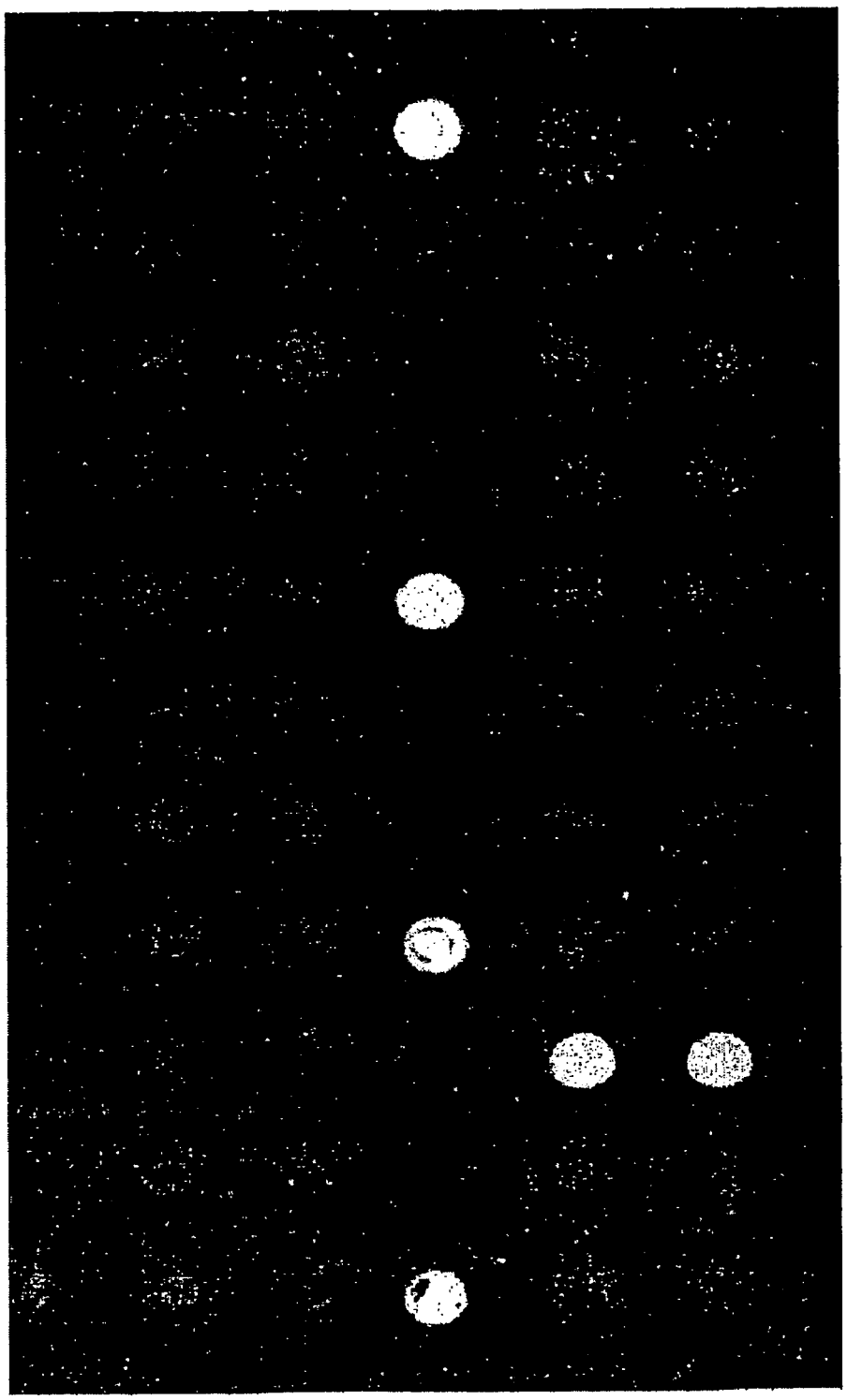
Figure 2F:
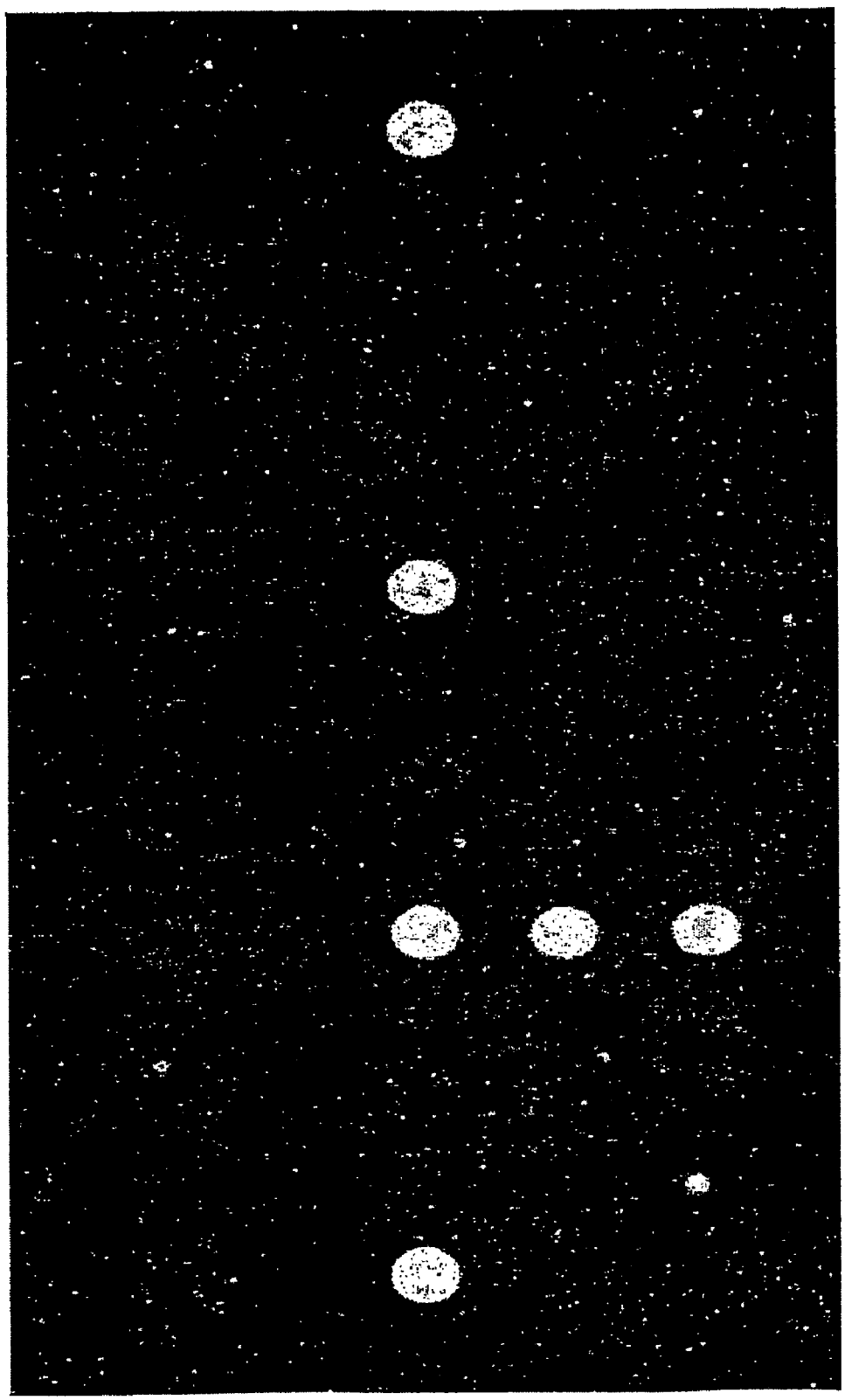

The genotyping kit of the invention for diagnosis of human papillomavirus (HPV) infection comprises: a DNA chip with probes that have nucleotide sequences complementary to DNA of HPV; primers for amplifying DNA obtained from clinical samples by PCR; and means for labeling amplified DNA hybridized with the probes of the said DNA chip.

The present inventors have tried to detect HPV infection and identify the types of HPV by way of genotyping DNA from clinical samples and prepared probes that have nucleotide sequences complementary to the DNA of HPV, and a DNA chip including the said probes. Further, we prepared an HPV genotyping kit comprising a DNA chip including probes that have nucleotide sequences complementary to the DNA of HPV, primers for amplifying DNA obtained from clinical samples by PCR, and means for labeling amplified DNA hybridized to the probes of the said DNA chip, and we successfully detected HPV infection and identified genotypes of infecting HPV with the aid of the genotyping kit in a simple and accurate manner.

The present invention provides nucleotide sequences of HPV DNA, preferably nucleotide sequences complementary to the L1 region of HPV DNA as probes. The probes of the present invention comprise nucleotide sequences set forth in SEQ ID NO: 1-30 (Tables 1a and 1b). In Table 1, the underlined regions on SEQ ID NO: 25 are additional sequences to provide the conformation suitable for the function of probes.

TABLE 1a

Probes for newly added HPV Types

| SEQ ID NO. | HPV Type | Sequence |
|---|---|---|
| 1 | 13 | 5'-ACATCATCTCTTTCAGACACATATAAGGCC-3' |
| 2 | 26 | 5'-AGTACATTATCTGCAGCATCTGCATCCACT-3' |
| 3 | 30 | 5'-TTATCCACATATAATTCAAGCCAAATTAAA-3' |
| 4 | 43 | 5'-CCTCTACTGACCCTACTGTGCCCAGTACAT-3' |
| 5 | 53 | 5'-TCTACATATAATTCAAAGCAAATTAAACAGTA-3' |
| 6 | 54 | 5'-TACAGCATCCACGCAGGATAGCTTTAATAAT-3' |
| 7 | 54 | 5'-CATCCACGCAGGATAGCTTTAATAATTCTG-3' |
| 8 | 55 | 5'-TGTGCTGCTACAACTCAGTCTCCATCTACAACA-3' |
| 9 | 57 | 5'-GAAACTAATTATAAAGCCTCCAATTATAAGGAA-3' |
| 10 | 61 | 5'-CTGTATCTGAATATAAAGCCACAAGCTTTAG-3' |
| 11 | 61 | 5'-CCTGTATCTGAATATAAAGCCACAAGCTTT-3' |
| 12 | 62 | 5'-CCTCCACTGCTGCAGCAGAATACACGGCTA-3' |
| 13 | 64 | 5'-TACAAATCCACCATATGCAAACACTAATTTTAA-3' |
| 14 | 67 | 5'-TATGTTCTGAGGAAAAATCAGAGGCTACAT-3' |
| 15 | 68 | 5'-TTTGTCTACTACTACTGAATCAGCTGTACCAAA-3' |
| 16 | 69 | 5'-AATCTGCATCTGCCACTTTTAAACCATCAGATT-3' |
| 17 | 70 | 5'-AACGGCCATACCTGCTGTATATAGCCCTAC-3' |
| 18 | 70 | 5'-ACCGAAACGGCCATACCTGCTGTATATAGC-3' |
| 19 | 74 | 5'-CGCCTTCTGCTACATATAATAGTTCAGACT-3' |
| 20 | JC9710 | 5'-AAACACCCTCTGACACATACAAGGCTTCCA-3' |
| 21 | 16 | 5'-GTGCTGCCATATCTACTTCAGAAACTACAT-3' |
| 22 | 16 | 5'-TATGTGCTGCCATATCTACTTCAGAAACTACATA-3' |
| 23 | 34 | 5'-GGTACACAATCCACAAGTACAACTGCACCA-3' |
| 24 | 35 | 5'-TTCTGCTGTGTCTTCTAGTGACAGTACATA-3' |
| 25 | 35 | 5'-<u>GCACG</u>GTCTGTGTGTTCTGCTGTGTCTTCTA<u>CGTGC</u>-3' |
| 26 | 40 | 5'-CTTATGTGCTGCCACACAGTCCCCCACACC-3' |
| 27 | 56 | 5'-TATTAGTACTGCTACAGAACAGTTAAGTAA-3' |
| 28 | 58 | 5'-CACTGAAGTAACTAAGGAAGGTACATATAA-3' |
| 29 | 59 | 5'-TCTACTACTTCTTCTATTCCTAATGTATAC-3' |
| 30 | 66 | 5'-CTAAAAGCACATTAACTAAATATGATGCCC-3' |

TABLE 1b

| | | |
|---|---|---|
| 31 | 6 | 5'-ATCCGTAACTACATCTTCCACATACACCAA-3' |
| 32 | 11 | 5'-ATCTGTGTCTAAATCTGCTACATACACTAA-3' |
| 33 | 18 | 5'-TGCTTCTACACAGTCTCCTGTACCTGGGCA-3' |
| 34 | 31 | 5'-TGTTTGTGCTGCAATTGCAAACAGTGATAC-3' |
| 35 | 33 | 5'-TTTATGCACACAAGTAACTAGTGACAGTAC-3' |
| 36 | 39 | 5'-TCTACCTCTATAGAGTCTTCCATACCTTCT-3' |
| 37 | 42 | 5'-CTGCAACATCTGGTGATACATATACAGCTG-3' |
| 38 | 44 | 5'-GCCACTACACAGTCCCCTCCGTCTACATAT-3' |

TABLE 1b-continued

| 39 | 45 | 5'-ACACAAAATCCTGTGCCAAGTACATATGAC-3' |
|----|----|--------------------------------------|
| 40 | 51 | 5'-AGCACTGCCACTGCTGCGGTTTCCCCAACA-3' |
| 41 | 52 | 5'-TGCTGAGGTTAAAAAGGAAAGCACATATAA-3' |
| 42 | β-globin | 5'-TGCACCTGACTCCTGAGGAGAAGTCTGCCG-3' |
| 47 | 16 | 5'-GTCATTATGTGCTGCCATATCTACTTCAGA-3' |
| 48 | 34 | 5'-TACACAATCCACAAGTACAAATGCACCATA-3' |
| 49 | 35 | 5'-GTCTGTGTGTTCTGCTGTGTCTTCTAGTGA-3' |
| 50 | 40 | 5'-GCTGCCACACAGTCCCCCACACCAACCCCA-3' |
| 51 | 56 | 5'-GTACTGCTACAGAACAGTTAAGTAAATATG-3' |
| 52 | 58 | 5'-ATTATGCACTGAAGTAACTAAGGAAGGTAC-3' |
| 53 | 59 | 5'-CTGTGTGTGCTTCTACTACTGCTTCTATTC-3' |
| 54 | 66 | 5'-CTATTAATGCAGCTAAAAGCACATTAACTA-3' |

The probes of the present invention enable highly specific and sensitive detection of HPV infection and identification of the HPV genotype, and have higher specificity and sensitivity than the probes for HPV genotyping described in PCT/KR/01213 (filed on Oct. 26, 2000). Among the probes of the present invention, the probes set forth in SEQ ID NO: 1-20, HPV 13, 26, 30, 43, 53, 54, 55, 57, 61, 62, 64, 67, 68, 69, 70, 74, and JC9710 are not included in the genotyping kit described in the above application, and therefore the probes according to the present invention enable it to be an implement that can detect more various types of HPV, contributing to its accuracy. The probes for HPV genotyping described in PCT/KR/01213 further comprise additional probes for HPV 16, 34, 35, 40, 56, 58, 59, and 66, along with nucleotide sequences set forth in SEQ ID NO: 31-41.

The DNA chip of the present invention may comprise one or more HPV probes selected from nucleotide sequences set forth in SEQ ID NO: 1-30. In addition, it may further comprise a β-globin sequence as a marker, and preferably the nucleotide sequence set forth in SEQ ID NO: 42. In one embodiment of the invention, the DNA chip comprises DNA chips including all probe sequence sets that are easily combined by those skilled in the art. It includes the following.

Embodiment 1

A DNA chip comprising one or more HPV probes selected from the group consisting of oligonucleotides having nucleotide sequences set forth in SEQ ID NO: 1 to 30 and oligonucleotides having nucleotide sequences complementary to the said oligonucleotides.

Embodiment 2

A DNA chip comprising:
(i) one or more HPV probes selected from the group consisting of oligonucleotides having nucleotide sequences set forth in SEQ ID NO: 1 to 30 and oligonucleotides having nucleotide sequences complementary to the said oligonucleotides; and
(ii) one or more HPV probes selected from the group consisting of probes having nucleotide sequences set forth in SEQ ID NO: 31 to 41 and nucleotide sequences complementary to the said nucleotide sequences.

Embodiment 3

A DNA chip comprising:
(i) one or more HPV probes selected from the group consisting of probes having nucleotide sequences set forth in SEQ ID NO: 1 to 20 and nucleotide sequences complementary to the said nucleotide sequences;
(ii) 8 HPV probes selected from the group consisting of probes having nucleotide sequences set forth in SEQ ID NO: 21 to 30 and nucleotide sequences complementary to the said nucleotide sequences; and
(iii) 11 HPV probes having nucleotide sequences set forth in SEQ ID NO: 31 to 41 and nucleotide sequences complementary to the said nucleotide sequences.

Embodiment 4

A DNA chip comprising:
(i) 9 HPV probes selected from the group consisting of probes having nucleotide sequences set forth in SEQ ID NO: 4 to 10;
(ii) 8 HPV probes selected from the group consisting of probes having nucleotide sequences set forth in SEQ ID NO: 21 to 30 and nucleotide sequences complementary to the said nucleotide sequences; and
(iii) 11 HPV probes having nucleotide sequences set forth in SEQ ID NO: 31 to 41 and nucleotide sequences complementary to the said nucleotide sequences.

Embodiment 5

A DNA chip comprising:
(i) 3 HPV probes having nucleotide sequences set forth in SEQ ID NO: 4, 15, and 16;
(ii) 8 HPV probes selected from the group consisting of probes having nucleotide sequences set forth in SEQ ID NO: 21 to 30 and nucleotide sequences complementary to the said nucleotide sequences; and
(iii) 11 HPV probes having nucleotide sequences set forth in SEQ ID NO: 31 to 41 and nucleotide sequences complementary to the said nucleotide sequences.

In one embodiment of the invention, the DNA chip may further comprise position markers to locate probes. The position markers include, but are not limited to, β-globin, actin, and GAPDH (glyceraldehyde-3-phosphate dehydrogenase) genes, and the like. The preferable position marker is β-globin, whose sequence is set forth in SEQ ID NO: 42.

According to the present invention, probes that have nucleotides complementary to DNA of HPV are provided. The probes of the invention are characterized to specifically hybridize with DNA of HPV.

The process for preparing a DNA chip contained in the said HPV genotyping kit comprises the steps of: preparing 5' terminal amine-linked DNA probes which have nucleotide sequences complementary to DNA of HPV; affixing the DNA probes thus prepared to an aldehyde-derivatized solid surface; and reducing excessive aldehydes not reacted with amine. The process for preparing a DNA chip of the invention is described in more detail by the following steps.

Step 1: Preparation of Probes

5' terminal amine-linked DNA probes that have nucleotide sequences complementary to the DNA of HPV are prepared. The nucleotide sequences of the probes are designed and synthesized to have nucleotide sequences complementary to the DNA of HPV, preferably the L1 region of HPV DNA, and the probes are prepared by linking an amine group at the 5' terminal of the nucleotide sequences which enables the probes to bind to an aldehyde-derivatized solid surface.

Step 2: Affixture of Probes

DNA probes prepared in Step 1 are affixed to an aldehyde-derivatized surface of a solid support, preferably glass. The probes are affixed to the surface of the solid support via a Schiff's base reaction between an aldehyde group on the surface of the solid support and an amine group at the 5' terminal of the probe under the condition of a 30 to 40° C. temperature and 70 to 100% humidity, while controlling the concentration of probes in a range of preferably 100 to 300 pmol/μl, and more preferably 200 pmol/μl. Also, β-globin which functions as a control for position markers and the hybridization reaction are affixed to the surface of the solid support.

Step 3: Preparation of DNA Chip

Excessive aldehydes not reacted with the amine on the solid surface are reduced by employing a reducing agent of NaBH$_4$, to finally prepare a DNA chip.

The present invention also provides an HPV genotyping kit comprising the said DNA chip and a method for diagnosis of HPV infection using the said genotyping kit. The present invention relates to an HPV genotyping kit comprising:

(i) a DNA chip according to the invention;
(ii) primers for amplifying DNA obtained from clinical samples by PCR; and,
(iii) means for labeling amplified DNA hybridized with the said DNA chip.

The present invention also relates to a method for diagnosis of HPV infection comprising the steps of:

(i) amplifying DNA obtained from clinical samples by PCR with primers of the HPV genotyping kit, for example primers set forth in SEQ ID NO: 43 and 44;
(ii) applying the amplified DNA to the DNA chip of the HPV genotyping kit to hybridize the amplified DNA with probes of the DNA chip; and
(iii) detecting DNA bound on the surface of the DNA chip after labeling hybridized DNA.

In one embodiment according to the invention, amplification of sample DNA may be carried out via a usual PCR, preferably a two-step PCR or a multiplex PCR that amplifies using more than 2 primers at the same time, and more preferably a multiplex two-step PCR that amplifies in two steps using more than 2 primers.

The development of the best condition for the HPV DNA sequence amplification methodology resulted in the two-step PCR or the multiplex PCR.

PCR consists of pre-denaturation, denaturation, primer annealing, and chain extension.

While conventional PCR is performed by repeating one step under the same conditions, two-step PCR is performed with another amplification step, that is, two-step PCR is performed by repeating one or more steps among denaturation, primer annealing, or chain extension under different conditions. According to the present invention, the first amplification step is carried out for a shorter time than that of the conventional chain extension step, and the second amplification step is carried out for an even shorter time than that of the first amplification step. Therefore, it prevents obtaining lengthy products when the extension reaction is carried out for a longer time (e.g. 1 to 2 minutes), and thus increases the specificity of probes, which is preferable. More preferably, a chain extension of the PCR amplification may be carried out for 20 to 30 seconds in the first step, and for 10 to 15 seconds in the second step.

In the present invention, while it is possible to amplify the HPV primer sample, the β-globin sample, and a marker separately, one-step amplification using HPV primers set forth in SEQ ID NO: 43-44 and β-globin primers set forth in SEQ ID NO: 45-46 can be performed together. Otherwise, two-step PCR as mentioned above can also be done.

PCR amplification may be carried out using an HPV primer sample and a β-globin sample, respectively, or it may be carried out in one step or two steps using HPV primers set forth in SEQ ID NO: 43-44 and β-globin primers set forth in SEQ ID NO: 45-46, concomitantly.

In one preferred embodiment of the invention, PCR was performed in a PCR thermocycler containing the said primers and β-globin, dATP, dCTP, dGTP, dTTP, labeling materials, and Taq polymerase, and optionally BSA and DMSO, with 5 cycles of denaturation for 5 min at 94° C., denaturation for 1 min at 94° C., primer annealing for 2 min at 45~50° C., and extension for 20~30 sec at 72° C., followed by 35 cycles of denaturation for 1 min at 94° C., primer annealing for 2 min at 45~50° C. and extension for 10~15 sec at 72° C., and then further extension for 2 min at 72° C., resulting in obtaining labeled amplified DNA samples.

The method for diagnosis of HPV infection using HPV genotyping kit of the invention is further illustrated by the following steps.

Step 1: Amplification of Sample DNA

DNA obtained from clinical samples is amplified using the primers of the HPV genotyping kit, where polymerase chain reaction (PCR) employing biotin-16-dUTP is carried out to give biotin-containing amplified DNA. 4 primers for amplification are set forth in Table 2:

TABLE 2

| SEQ ID NO. | HPV Type | Sequence | Base Number |
|---|---|---|---|
| 43 | Gp5+ | 5'-TTTKTTACHGTKGTDGATACYAC-3' | 23 |
| 44 | Gp6+ | 5'-GAAAHATAAAYTGYAADTCATAYTC-3' | 25 |
| 45 | BG 1 | 5'-ATACAAGTCAGGGCAGAG-3' | 18 |
| 46 | BG 2 | 5'-CTTAAACCTGTCTTGTAACC-3' | 20 |

In Table 1, R(A, g): Y(C, T): M(A, C): K(g, T): S(g, C): W(A, T), V(A, C, g): H(A, T, C): B(g, T, C): D(g, A, T): N(A, g, V, T), which is well-known to those skilled in the art.

Primers for DNA amplifying composed of nucleotide sequences set forth in SEQ ID NO: 43 and 44 are provided, as well as novel β-globin primers composed of nucleotide sequences set forth in SEQ ID NO: 45 and 46.

Step 2: Hybridization

Amplified DNA thus obtained is applied to the DNA chip of the HPV genotyping kit and hybridized with the probes of the DNA chip.

Step 3: Detection

The amplified sample DNA hybridized with the probes are labeled with means for labeling and detected with a confocal laser scanner.

Means for labeling comprise, but are not limited to, Cy5, biotin-binding compound, Cy3, EDANS (5-(2'-aminoethyl) amino-1-naphthalene sulfuric acid), tetramethylrhodamine (TMR), tetramethylrhodamine isocyanate (TMRITC), x-rhodamine or Texas red. Preferably, Cy5 and biotin-binding compound can be used. Labeling materials are detected by a confocal laser scanner.

The HPV genotyping kit of the invention is an implement that can detect HPV infection in a simple and accurate manner, as well as identify the types of infecting HPV, and therefore it may contribute to early diagnosis, prevention, and treatment of cervical cancer.

The present invention is further shown in the following examples, which should not be taken to limit the scope of the invention. Particularly, though a DNA chip with 22 or 28 probes was prepared in the Examples described below, it is to be understood that the present invention is not limited by types and numbers of probes, but DNA chips using nucleotide sequences derived from HPV DNA and any variety of detection kits using the said DNA chips are intended to be included within the scope of the invention.

EXAMPLE 1

Preparation of Probes

Prevalent HPV types including 15 high-risk types (HPV type 16, 18, 31, 33, 35, 39, 45, 51, 52, 56, 58, 59, 66, 68, 69) and 7 low-risk types (HPV type 6, 11, 34, 40, 42, 43, 44) were selected, and genotype-specific probe β-globin for each HPV type possessing an amine group at the 5' terminal of the sequence was prepared for the detection of HPV genotypes. The nucleotide sequence of each probe is set forth in the Sequence List.

EXAMPLE 2

Preparation of DNA Chip

A DNA chip was prepared as follows: each probe prepared in Example 1 was dissolved in 3×SSC (45 mM sodium citrate, 0.45M NaCl, pH 7.0) at a concentration of 200 pmol/μl, and spotted onto an aldehyde-derivatized silylated slide (CSS-100, CEL, Houston, Tex., USA) to form an array of spots with a size of 150 μm at 300 μm of spacing between spots using a microarrayer (GMS 417 Arrayer, TaKaRa, Japan), followed by performing a Schff's base reaction under the condition of a 37° C. temperature and over 70% humidity, for 4 hours. The slide was washed with 0.2% (w/v) sodium dodecyl sulfate (SDS), and with triple-distilled water. Then the slide was treated with a NaBH$_4$ solution (0.1 g NaBH$_4$, 30 ml phosphate buffered saline (PBS), 10 ml ethanol) for 5 minutes to reduce excessive aldehydes not reacted with amine, followed by washing with triple-distilled water and air-drying. Also, β-globin, which functions as a control group for position markers and the hybridization reaction, is affixed to the surface of the solid support.

EXAMPLE 3

Optimal PCR Amplification

To establish multiplex PCR and amplification of HPV genes from clinical samples, an Optimal HPV PCR was carried out under the following conditions:

3-1: Two-step PCR Amplification

Method 1

To obtain Cy5-labeled amplified DNA samples, PCR was performed with 5 cycles of denaturation for 5 min at 94° C., denaturation for 1 min at 94° C., primer annealing for 2 min at 50° C., and extension for 30 sec at 72° C., followed by 35 cycles of denaturation for 1 min at 94° C., primer annealing for 2 min at 50° C., and extension for 15 sec at 72° C., and then further extension for 2 min at 72° C.

Method 2

Cy5-linked amplified HPV DNA samples were prepared analogously as in Method 1, except for primer annealing for 30 sec at 50° C.

Method 3: Conventional One-step PCR of Prior Art

Cy5-labeled amplified DNA was obtained and compared after 40 cycles of denaturation for 5 min at 94° C., denaturation for 1 min at 94° C., primer annealing for 2 min at 50° C., and extension for 30 sec at 72° C., and then further extension for 2 min at 72° C.

Figure 4:
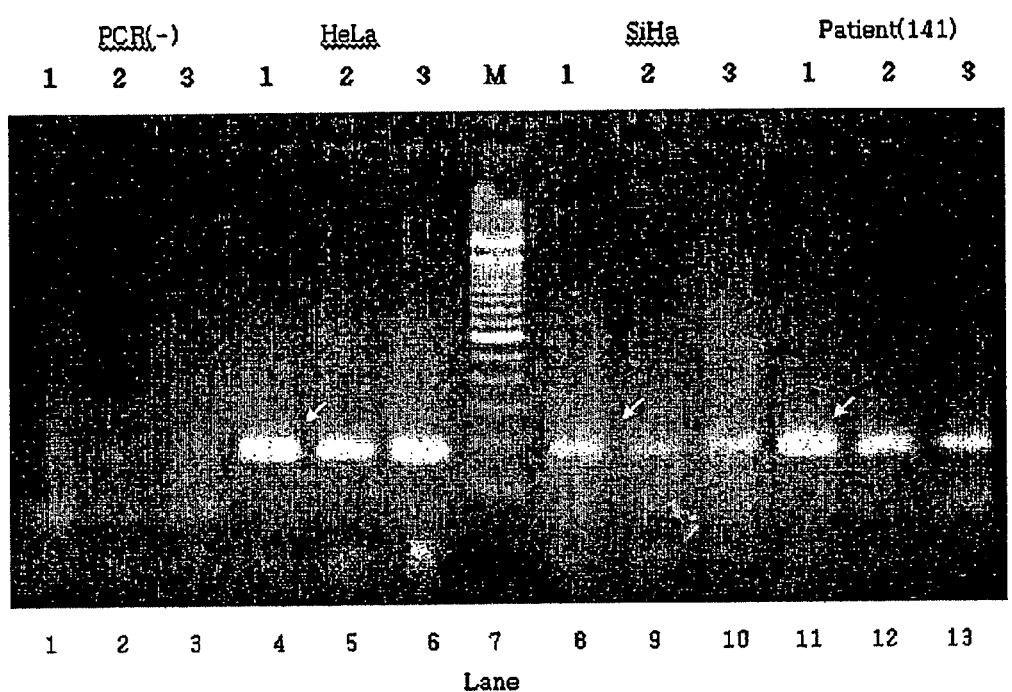
FIG. 4 is a photograph showing the result of DNA amplification by two-step PCR according to one preferred embodiment of the present invention.

When lanes 4~6, lanes 8~10, and lanes 11~13 in FIG. 4 were compared with one another, the conditions in methodology 2 (lanes 4, 8 and 11) were proven to be the most specific and efficient.

3-2: Multiplex PCR Amplification

The compositions and conditions for establishing multiplex PCR amplification of HPV are as follows.

In order to obtain Cy5-labeled amplified DNA samples, multiplex PCR using two-step PCR described in Example 3-1 was performed in a thermocycler (Perkin-Elmer Cetus, Calif., USA) with 50 μl of reaction mixture containing a 2×PCR buffer (50 mM KCl, 4 mM MgCl$_2$; 10 mM Tris-HCl; pH 8.3); 0.1 μg of DNA; 2~4 mM MgCl$_2$; 25 pmol of HPV primers set forth in SEQ ID NO: 43-44; 5 pmol of β-globin primers set forth in SEQ ID NO: 44-45; 40 μM each of dATP, dCTP, dGTP (Pharmacia); 30 μM of dTTP (Pharmacia); 0.5 μM Cy5-dUTP (NEN, USA); 2 units of Taq polymerase (TaKaRa, Japan); and optionally BSA and DMSO, with 5 cycles of denaturation for 5 min at 94° C., denaturation for 1 min at 94° C., primer annealing for 2 min at 45~50° C., and extension for 20~30 sec at 72° C., followed by 35 cycles of denaturation for 1 min at 94° C., primer annealing for 2 min at 45~50° C. and extension for 10~15 sec at 72° C., and then further extension for 2 min at 72° C.

Figure 5:
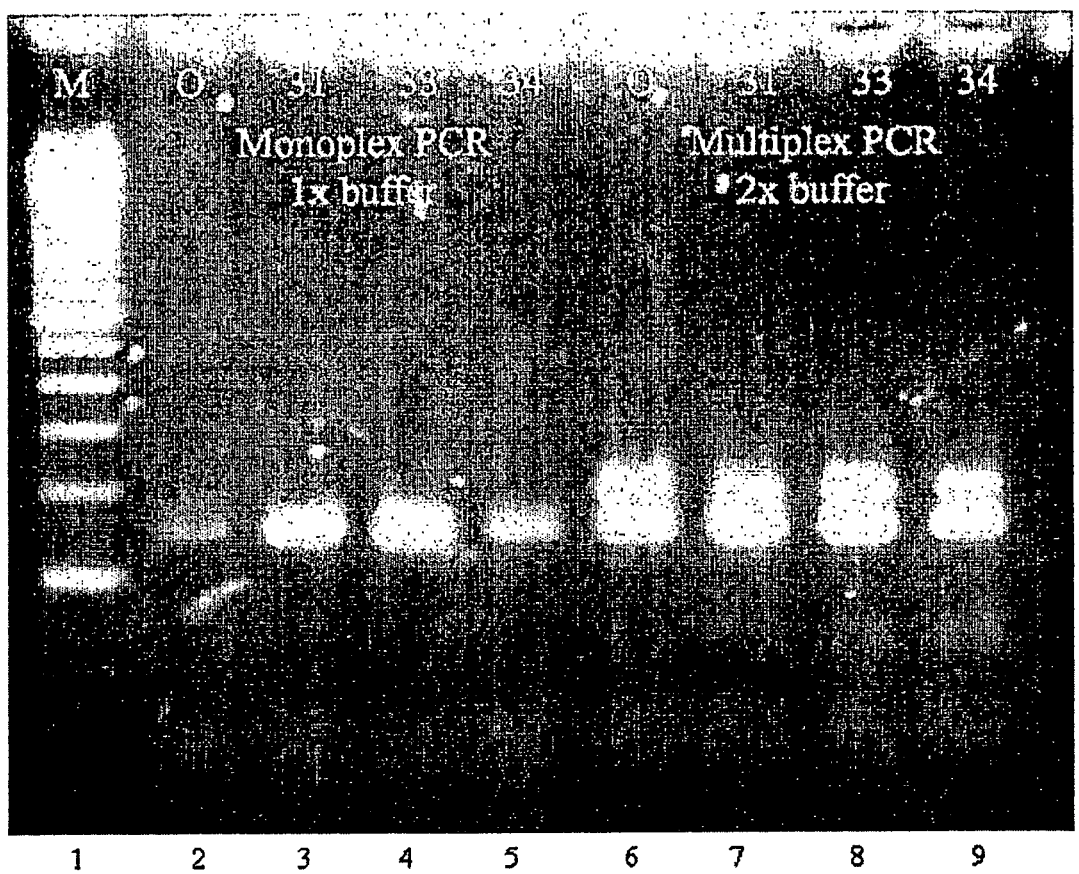
FIG. 5 is a photograph showing the result of DNA amplification by multiplex PCR according to one preferred embodiment of the present invention.
Figure 6:
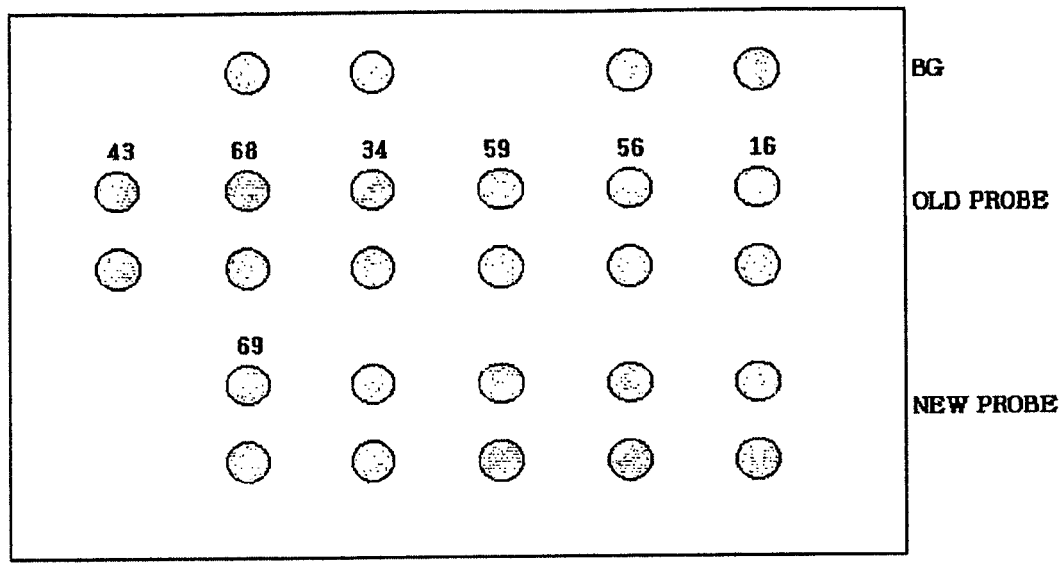
FIG. 6 is a schematic representation of the types and positions of the probes of the present invention and the probes of prior art.
Figure 7A:
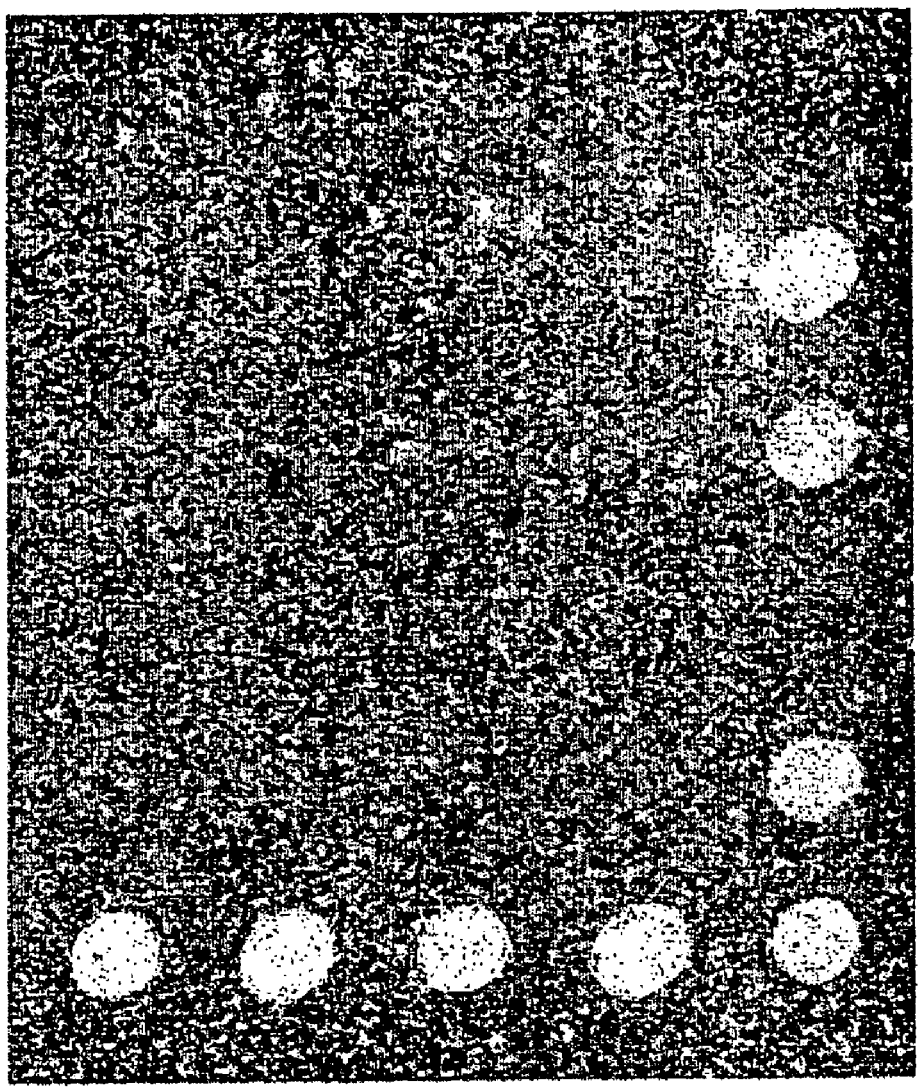
FIG. 7a is a photograph showing the result of HPV 16 DNA analysis using the DNA chip shown in FIG. 6.
Figure 7B:
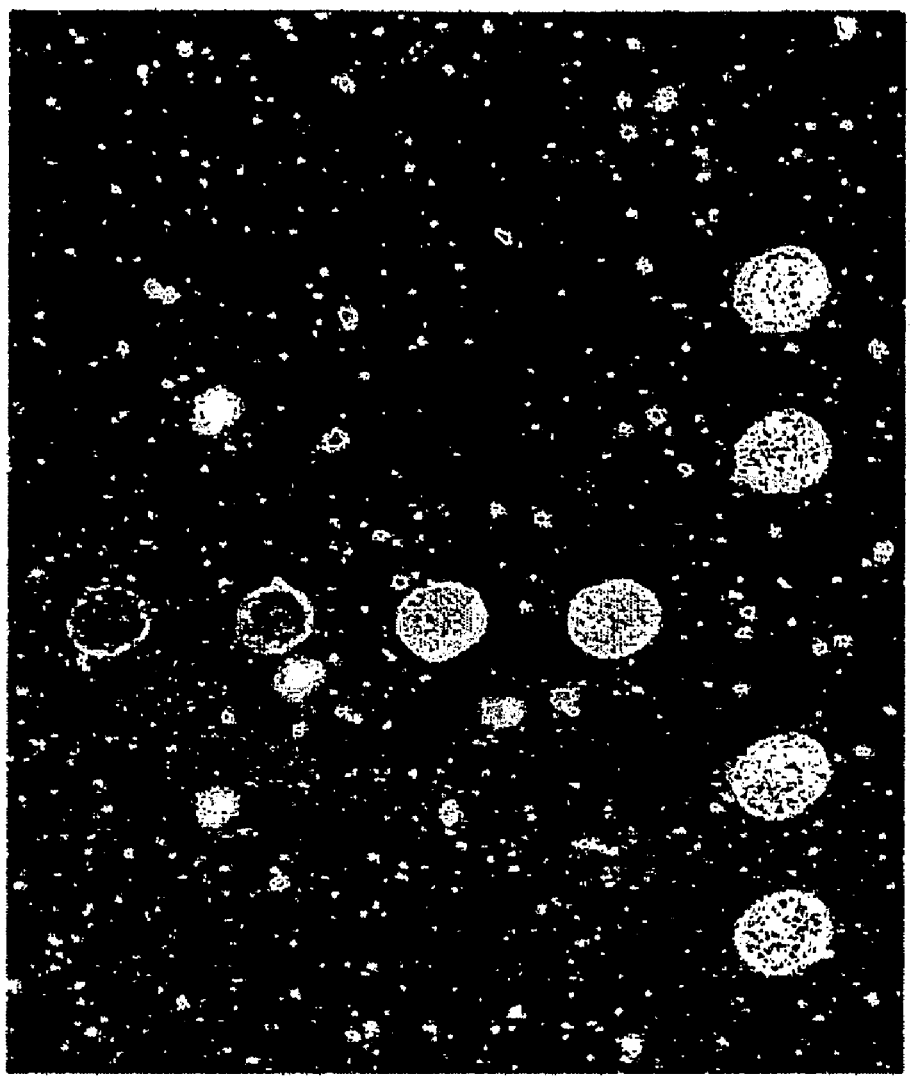
FIG. 7b is a photograph showing the result of HPV 18 DNA analysis using the DNA chip shown in FIG. 6.
Figure 7C:
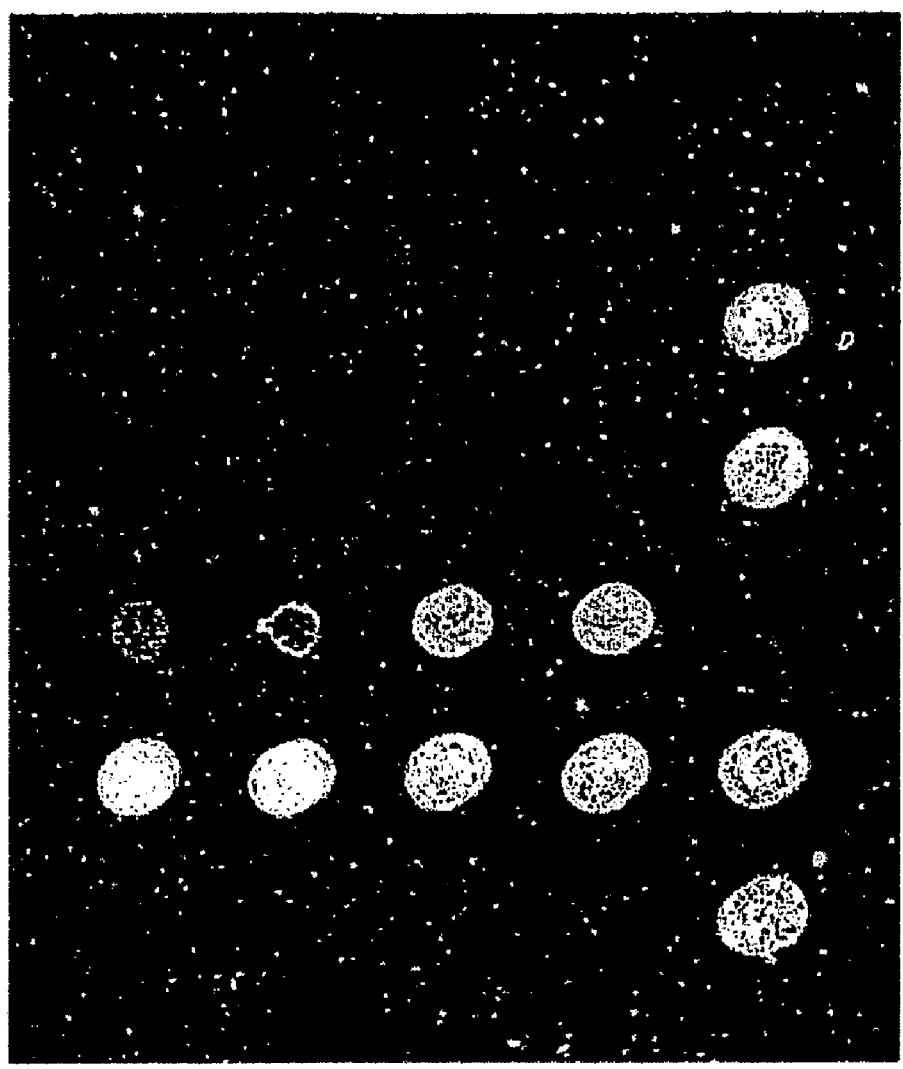
FIG. 7c is a photograph showing the result of HPV 56 DNA analysis using the DNA chip shown in FIG. 6.
Figure 7D:
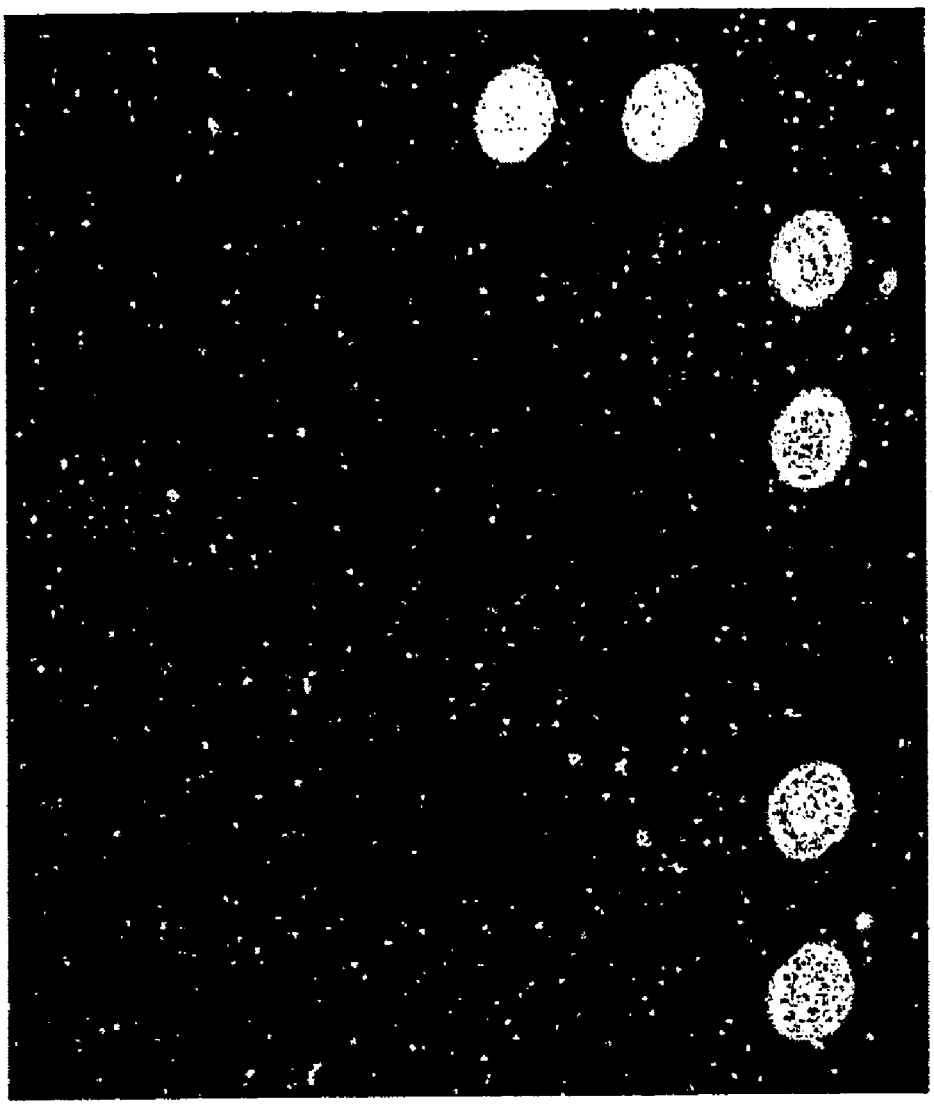
FIG. 7d is a photograph showing the result of HPV 43 DNA analysis using the DNA chip shown in FIG. 6.
Figure 7E:
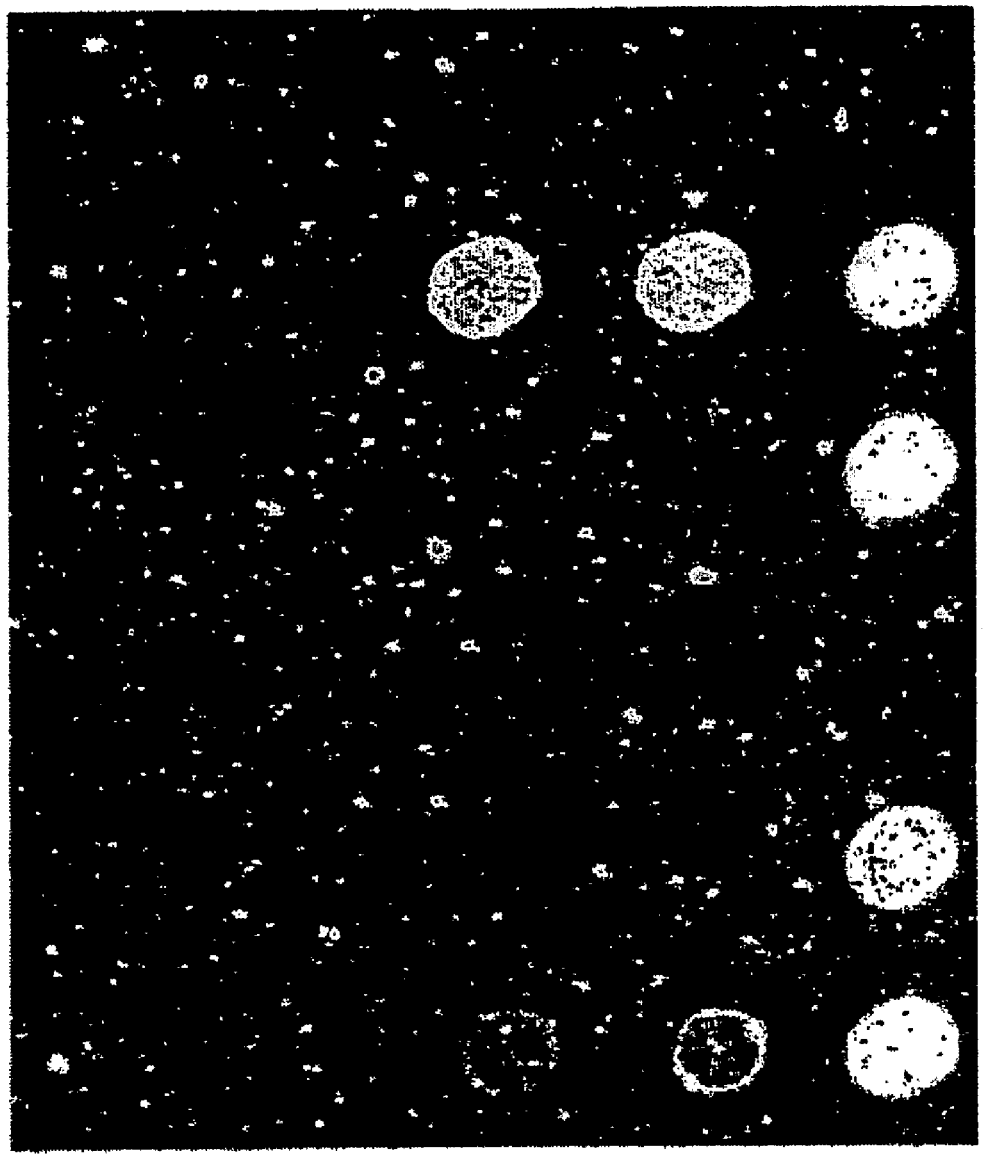
FIG. 7e is a photograph showing the result of HPV 68 DNA analysis using the DNA chip shown in FIG. 6.

When lanes 2~5 and lanes 6~9 in FIG. 5 were compared, HPV amplification efficiencies of 1×PCR buffer monoplex PCR and of 2×PCR buffer multiplex PCR were similar, and so the 2×PCR buffer multiplex PCR condition was found to be the most specific and efficient.

EXAMPLE 4

Preparation of Samples

In order to detect HPV infection in human cervical swabs, DNA was extracted from the said specimen and then purified. To test the adequacy of sample DNA, purified DNA was PCR amplified with β-globin primers set forth in SEQ ID NO: 45 and 46. The DNA samples which revealed β-globin DNA amplification were selected and used for further analyses of HPV DNA.

As HPV DNA standards, plasmid DNA comprising the HPV sequence obtained from the following distributors were used: HPV types 6, 11, 26, 40, 45, 51 and 57 (Dr. Ethel-Michele de Villiers, Angewandte Tumorvirologie, Deutsches Krebsforschungszentrum, Im Neuenheimer Feld 242, 69009 Heidelberg, Germany); HPV types 35, 44, and 56 (Dr. Attila Lörincz, Vice President, R&D and Scientific Director, Digene Diagnostics, Inc., 2301-B Broadbirch Drive, Silver Spring, Md. 20904, USA); HPV types 42, 58, 59, 61, 64 and 67 (Dr. Toshihiko Matsukura, Department of Pathology and Laboratory of Pathology, AIDS Research Center, National Institute of Infectious Disease, Tokyo 162, Japan); and HPV types 33, 34, 39, 52, 54, 66 and 70 (Dr.

Gérard Orth, Unité Mixte Institut Pasteur/INSERM (U. 190), Institut Pasteur, 25 rue du Docteur Roux, 75724 Paris Cedex 15, France).

Additionally, DNA extracted and purified from the following cell lines were used as positive controls: SiHa cell line (HPV 16, KCLB 30035, Human squamous carcinoma, cervix), purchased from Korean Cell Line Bank (Seoul National University, College of Medicine, Seoul, Korea).

The selected samples of DNA described above were PCR amplified using primers set forth in SEQ ID NO: 43 and 44.

EXAMPLE 4-1

Preparation of Positive Control Samples

To obtain Cy5-labeled amplified DNA samples, HPV 16 and HPV 18 DNA purified above were amplified by PCR with primers set forth in SEQ ID NO: 43 and 44. PCR was performed in a thermocycler (Perkin-Elmer Cetus, Calif., USA) with 50 μl of a reaction mixture containing a 1×PCR buffer (50 mM KCl, 4 mM $MgCl_2$, 10 mM Tris-HCl, pH 8.3); 0.1 μg of DNA; 4 mM $MgCl_2$; 25 pmol of each primer, 40 μM each of dATP, dCTP, and dGTP (Pharmacia); 30 μM of dTTP (Pharmacia); 0.05 μM Cy5-dUTP (NEN, USA); and 2 unit of Taq polymerase (TaKaRa, Japan) with 5 cycles of denaturation for 5 min at 94° C., denaturation for 1 min at 94° C., primer annealing for 2 min at 50° C., and extension for 30 sec at 72° C., followed by 35 cycles of denaturation for 1 min at 94° C., primer annealing for 2 min at 50° C. and extension for 15 sec at 72° C., and then extension for 2 min at 72° C.

EXAMPLE 4-2

Preparation of HPV Standards

Cy5-linked amplified HPV DNA samples were prepared analogously as in Example 4-1, except for employing templates of various HPV plasmids described above.

EXAMPLE 4-3

Preparation of Sample DNA from Clinical Samples

Cy5-linked amplified DNA samples were obtained analogously as in Example 4-1, except that DNA obtained from uterine cervical swabs were used as templates, and primers set forth in SEQ ID NO: 43 and 44 were employed as primers.

EXAMPLE 5

Detection of HPV Infection Using DNA Chip

Amplified DNA samples obtained in Example 4 were applied to the DNA chip prepared in Example 2, and hybridization was carried out in a hybridization reaction chamber made up of a Cover slip (GRACE Bio-Labs, USA, PC4L-1.0) with a 100 μl capacity.

As for the quantity of hybridization reaction samples, 10 μl each of amplified product was used for positive controls and plasmid DNA, and a mixture of 10 μl of HPV amplified product and 5 μl of beta-globin amplified product was used for DNA obtained from cervical swabs. The said reaction samples were denatured by adding 3N NaOH solution (10% v/v) and standing them for 5 min at room temperature, and neutralized by adding 1 M Tris-HCl (pH 7.2, 5% v/v) followed by 3N HCl (10% v/v) and cooling them for 5 min on ice. The samples were then mixed with a hybridization solution made up of a 6×SSPE (saline-sodium phosphate-EDTA buffer, Sigma Chemical Co., St. Louis, Mo., USA) and 0.2% SDS (sodium dodecyl sulfate), and applied onto the DNA chip. The hybridization reaction was carried out for 2 hours at 40° C., followed by washing with a 3×SSPE for 2 min and a 1×SSPE for 2 min, and air-drying at room temperature or spin-dryer drying.

The DNA chip hybridized with sample DNA was analyzed for fluorescent signals (extinction 650 nm, emission 668 nm) by using a confocal laser scanner (GSI Lumonics, Germany) (see: FIG. 1, FIGS. 2a-2l and FIGS. 3a-3j).

Figure 2G:
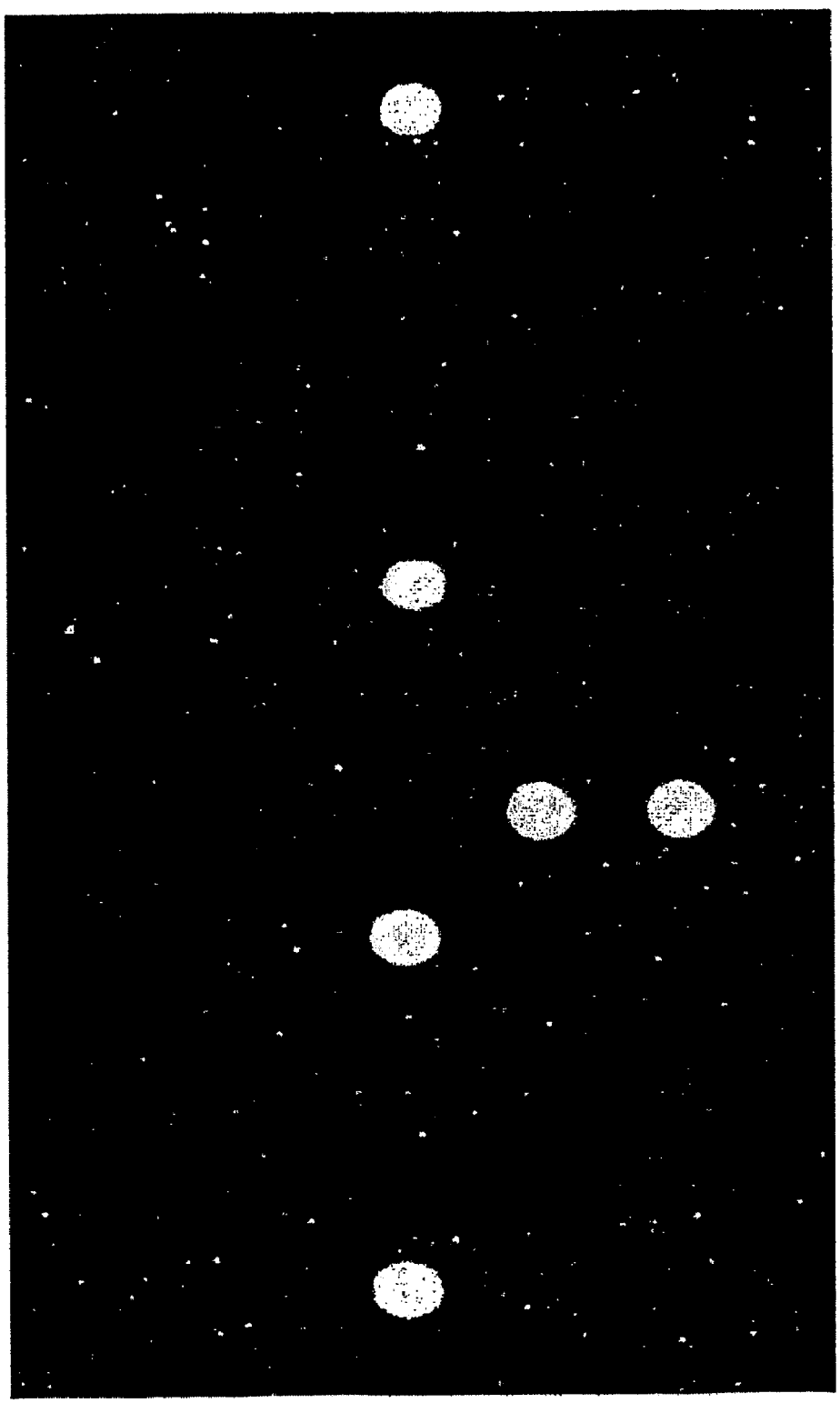
Figure 2H:
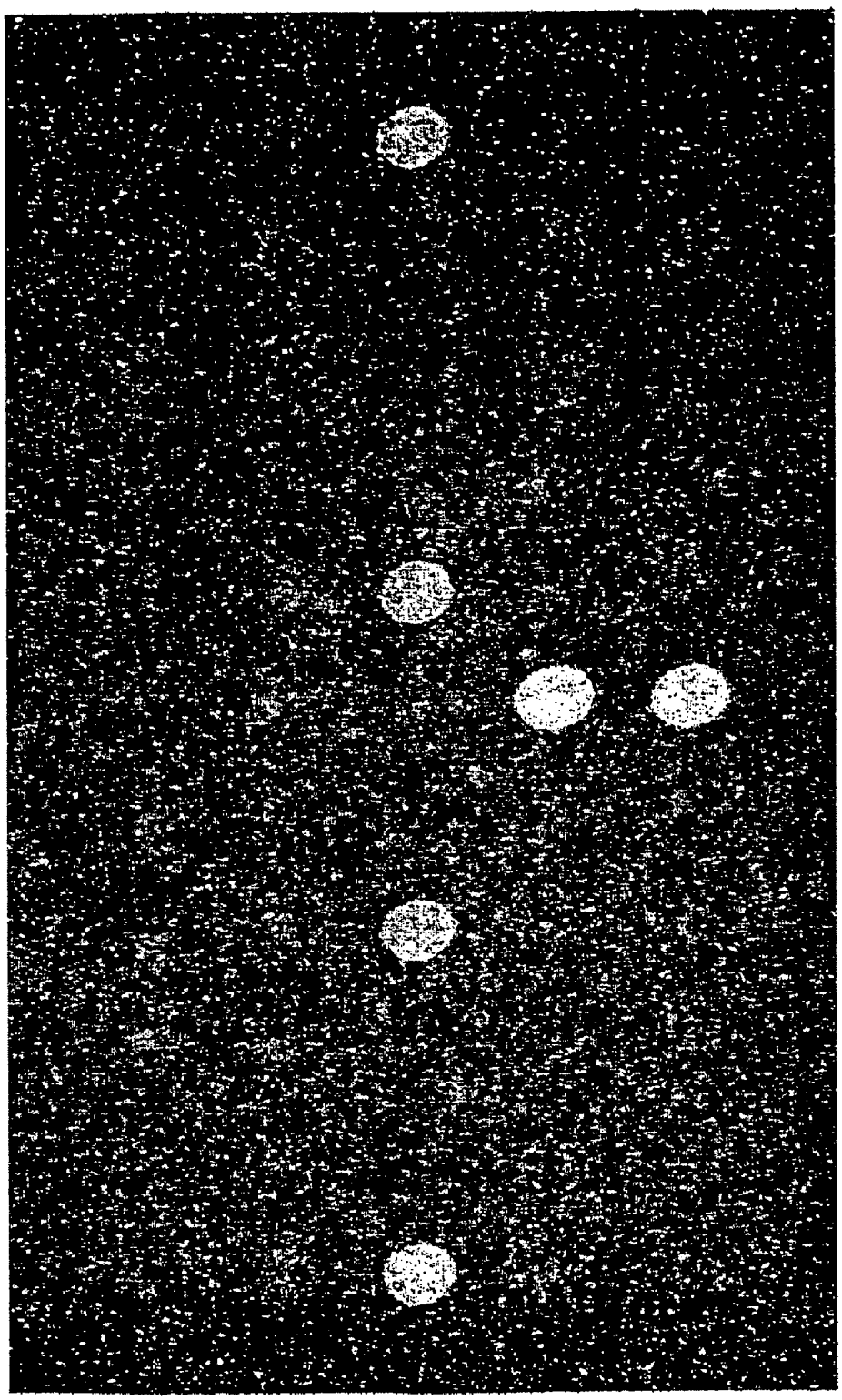
Figure 21:
Figure 2J:
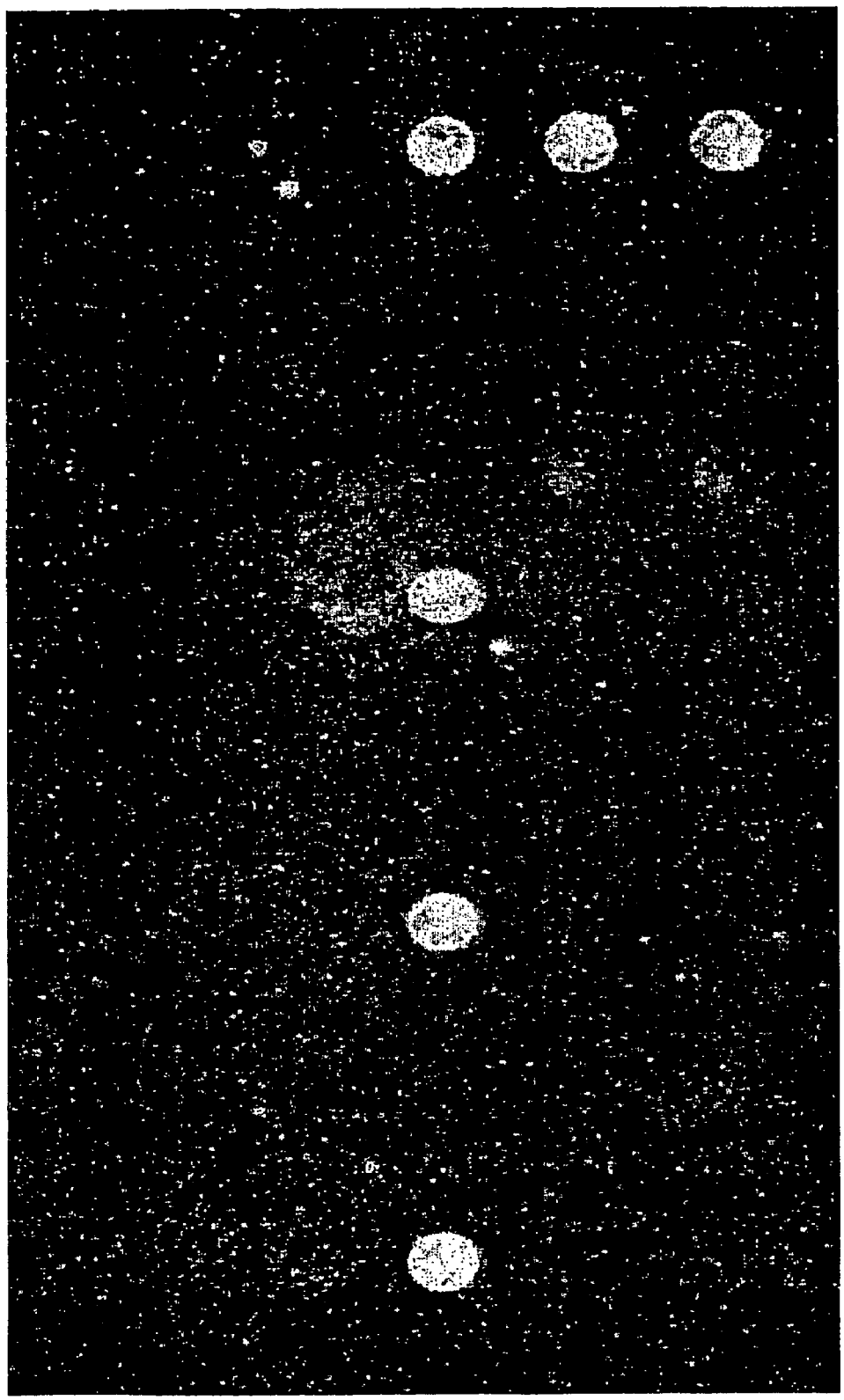
Figure 2K:
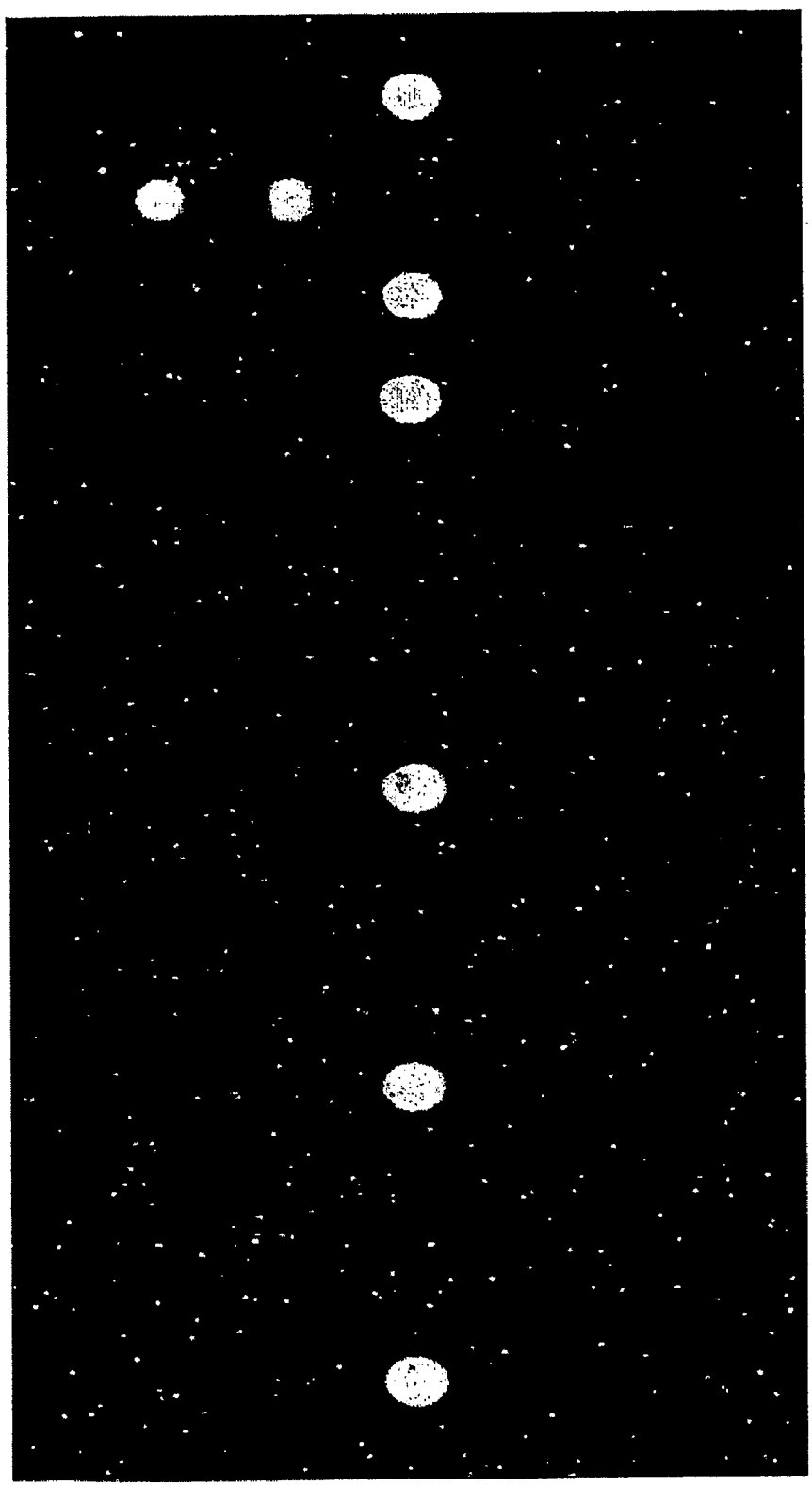
FIG. 2k is a photograph showing the result of HPV 61 DNA analysis using the DNA chip shown in FIG. 1b.
Figure 2L:
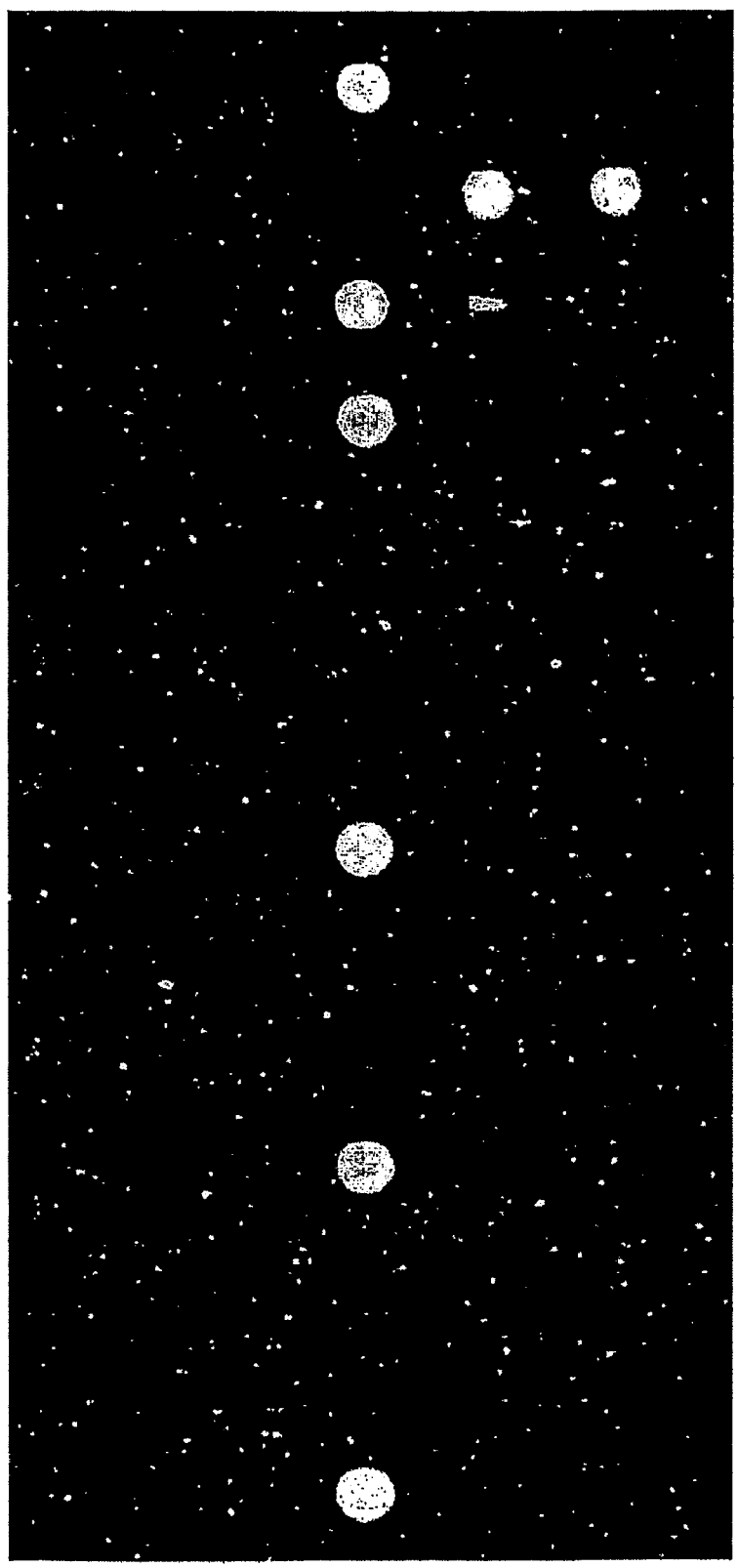
FIG. 2l is a photograph showing the result of HPV 67 DNA analysis using the DNA chip shown in FIG. 1b.
Figure 3A:
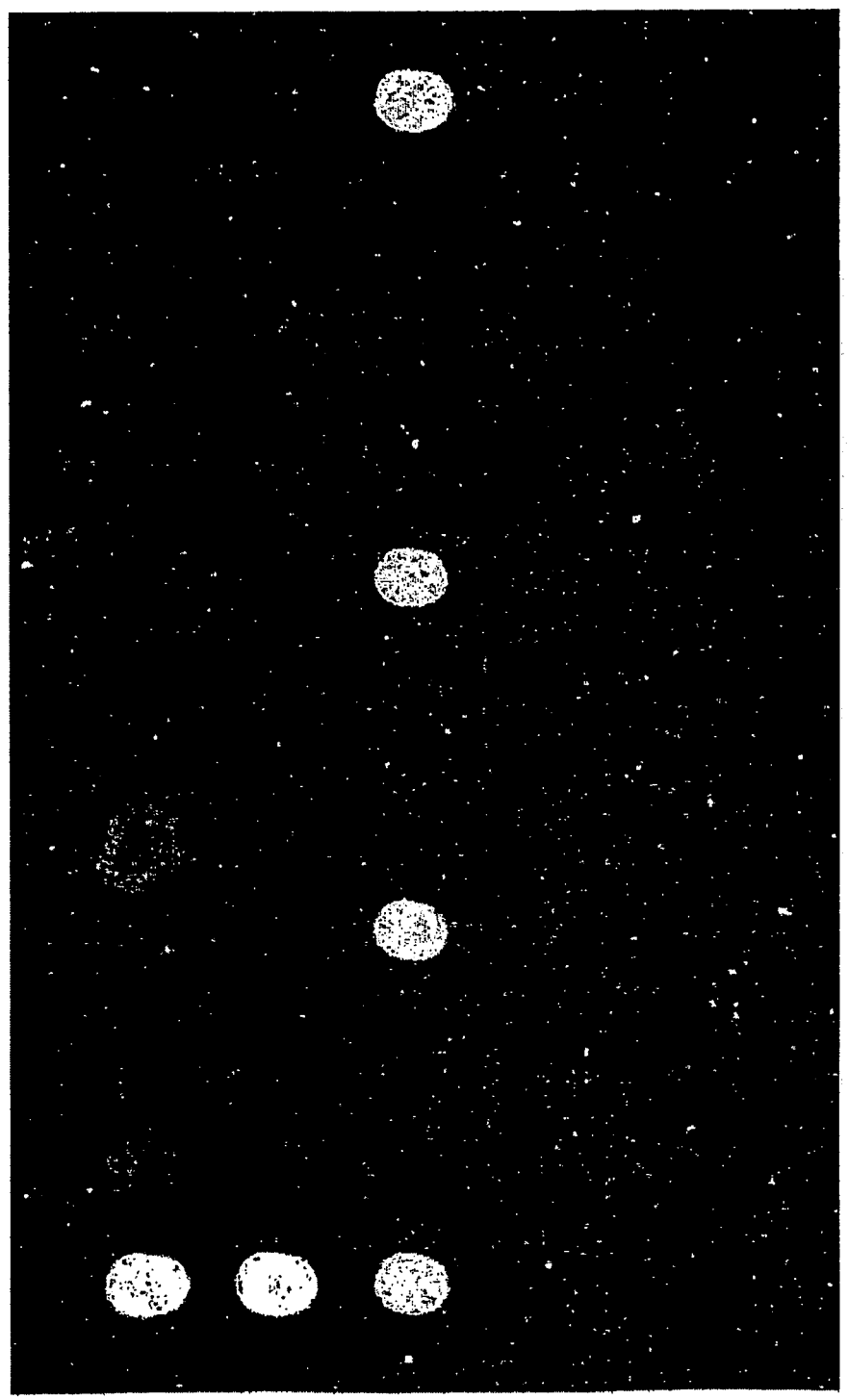
FIG. 3a is a photograph showing the result of analyzing a sample infected with HPV 16 using the DNA chip of the present invention.
Figure 3B:
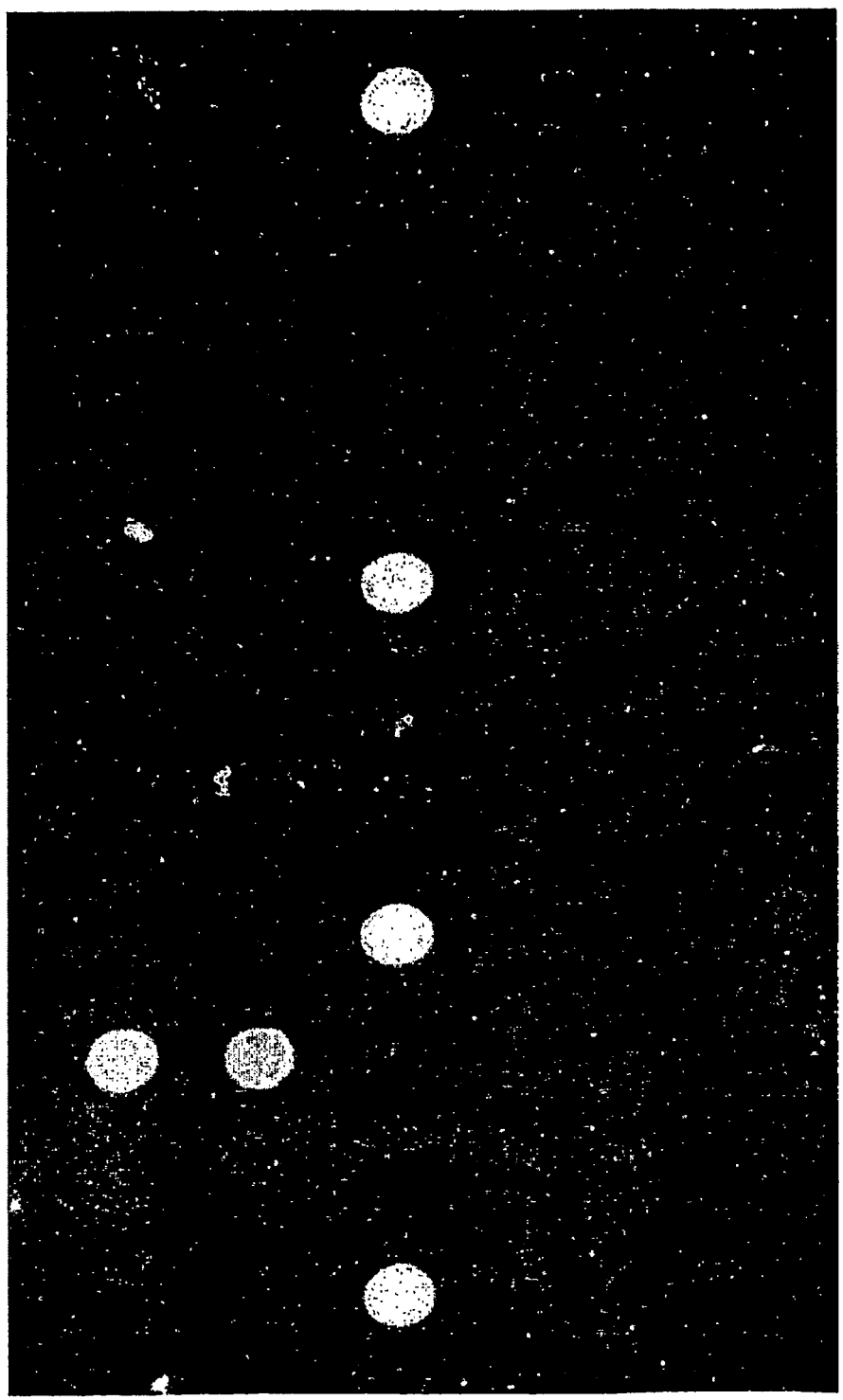
FIG. 3b is a photograph showing the result of analyzing a sample infected with HPV 31 using the DNA chip of the present invention.
Figure 3C:
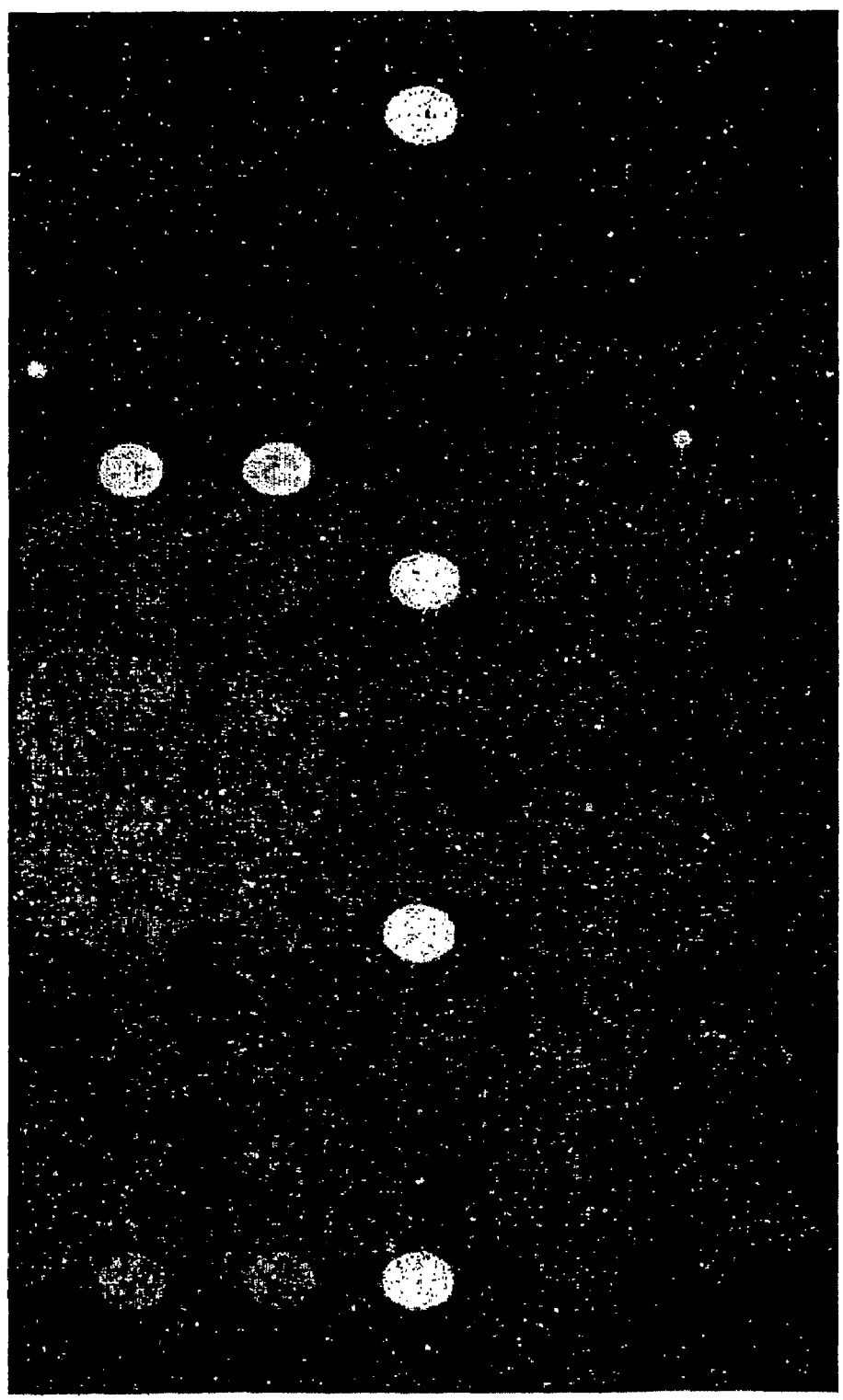
FIG. 3c is a photograph showing the result of analyzing a sample infected with HPV 51 using the DNA chip of the present invention.
Figure 3D:
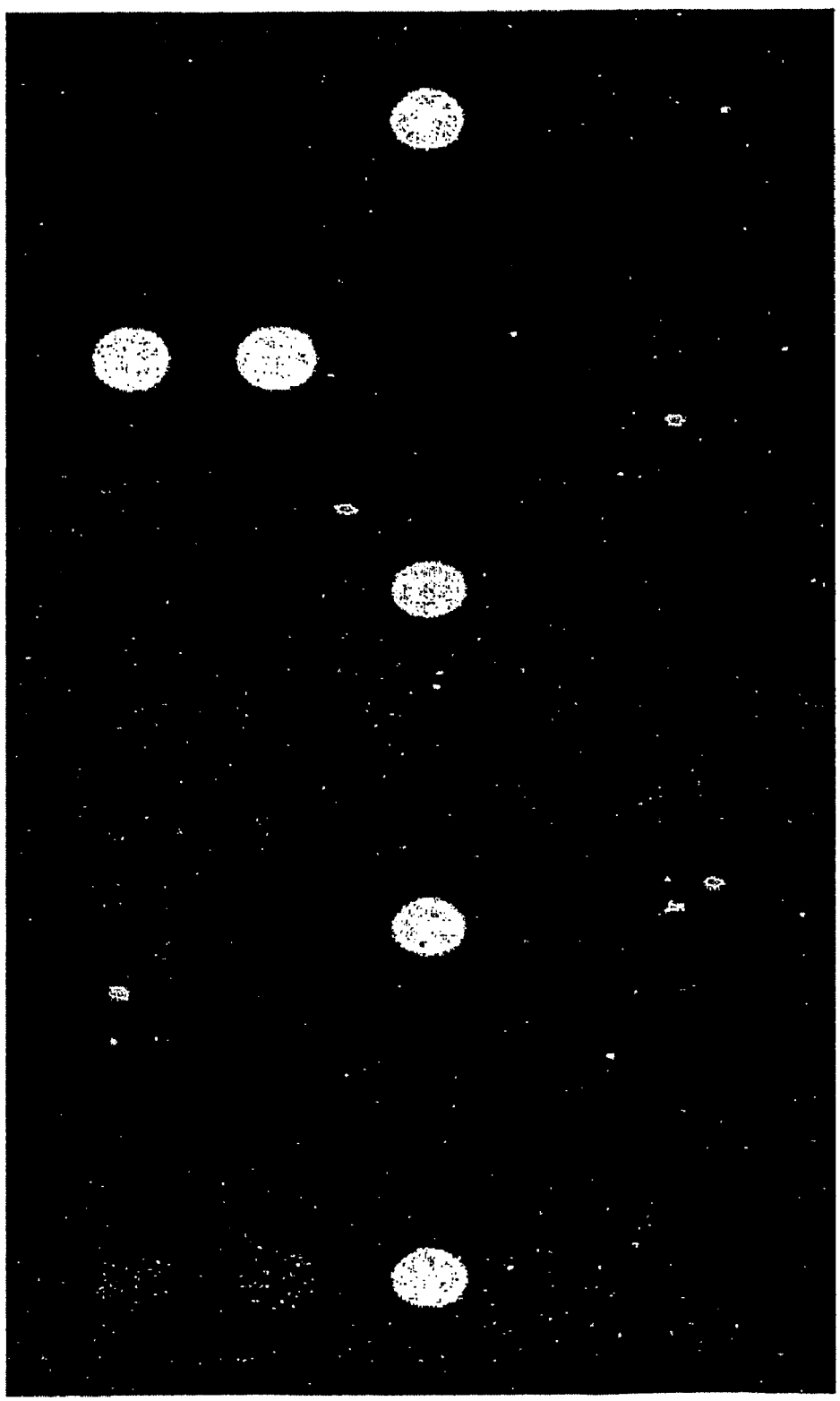
FIG. 3d is a photograph showing the result of analyzing a sample infected with HPV 52 using the DNA chip of the present invention.
Figure 3E:
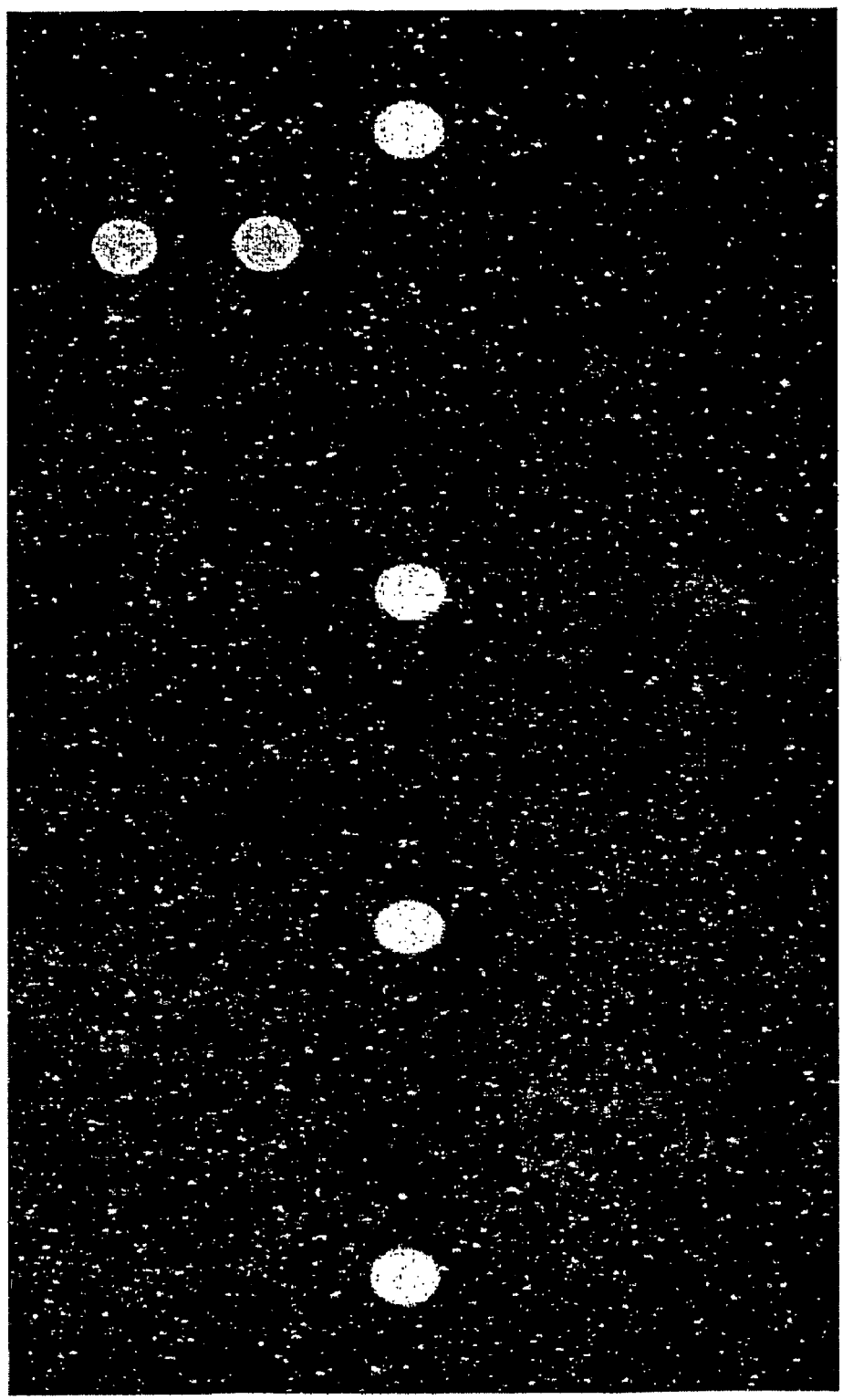
FIG. 3e is a photograph showing the result of analyzing a sample infected with HPV 56 using the DNA chip of the present invention.
Figure 3F:
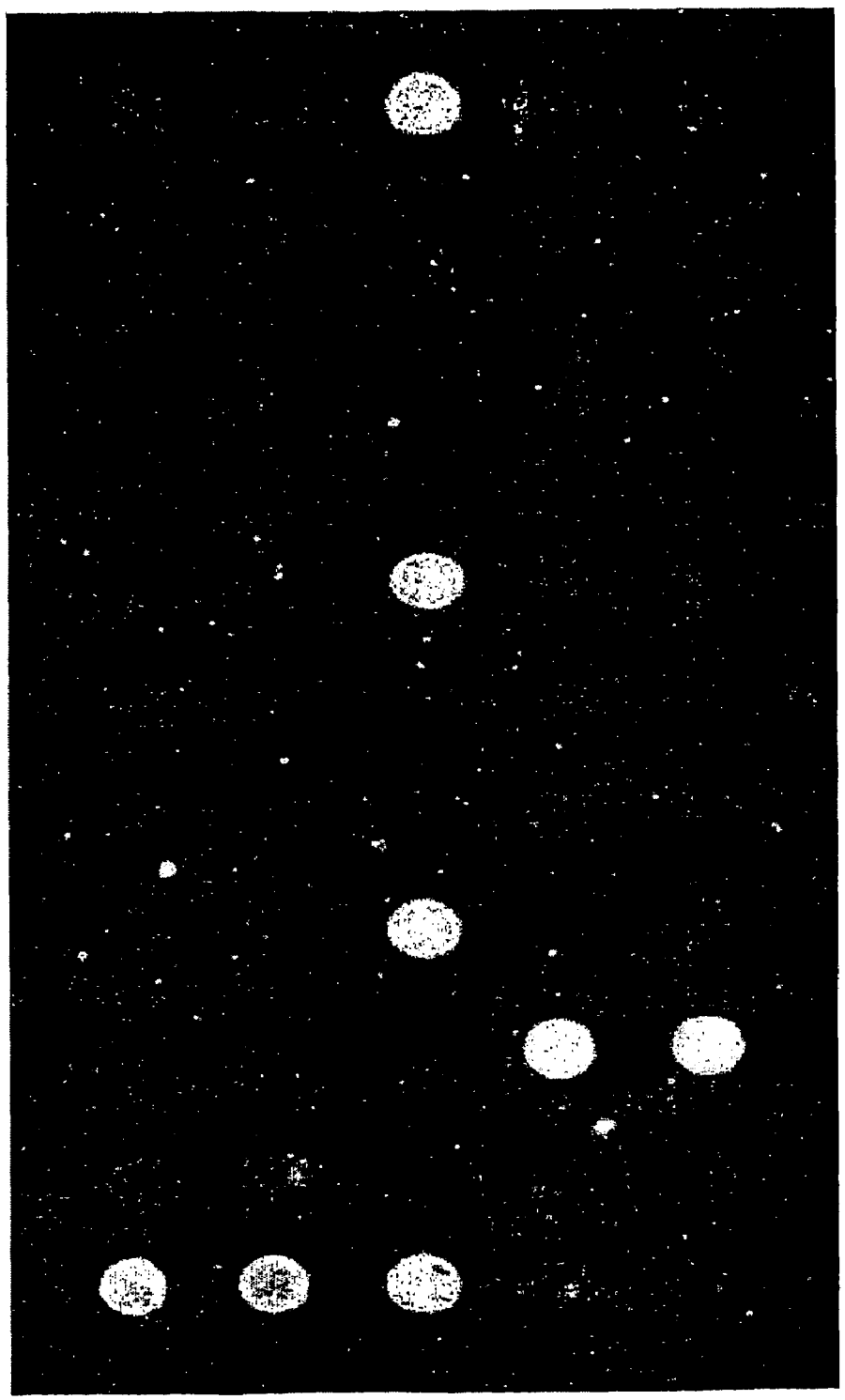
FIG. 3f is a photograph showing the result of analyzing a sample double-infected with HPV 16 and HPV 68 using the DNA chip of the present invention.
Figure 3G:
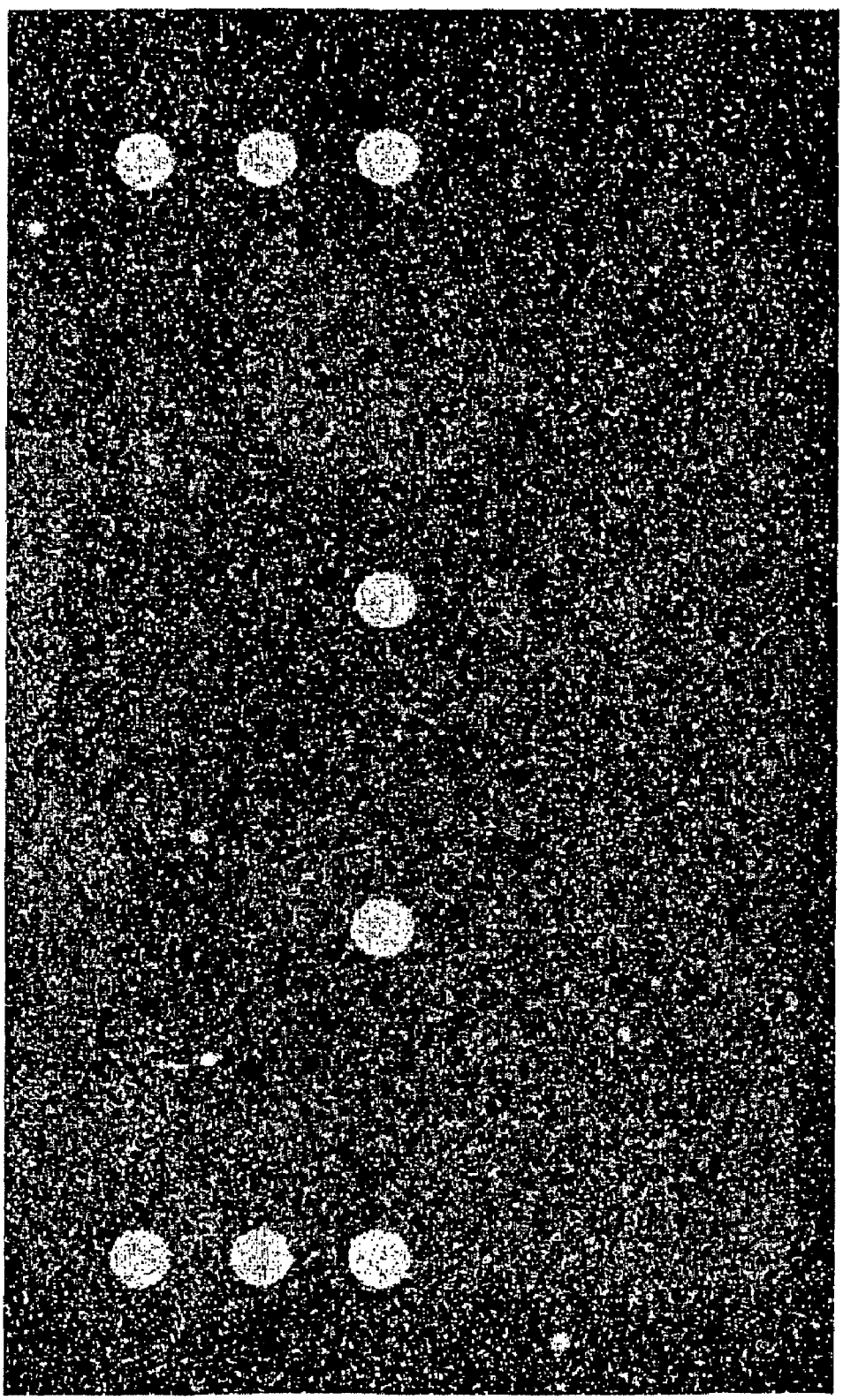
FIG. 3g is a photograph showing the result of analyzing a sample double-infected with HPV 16 and HPV 58 using the DNA chip of the present invention.
Figure 3H:
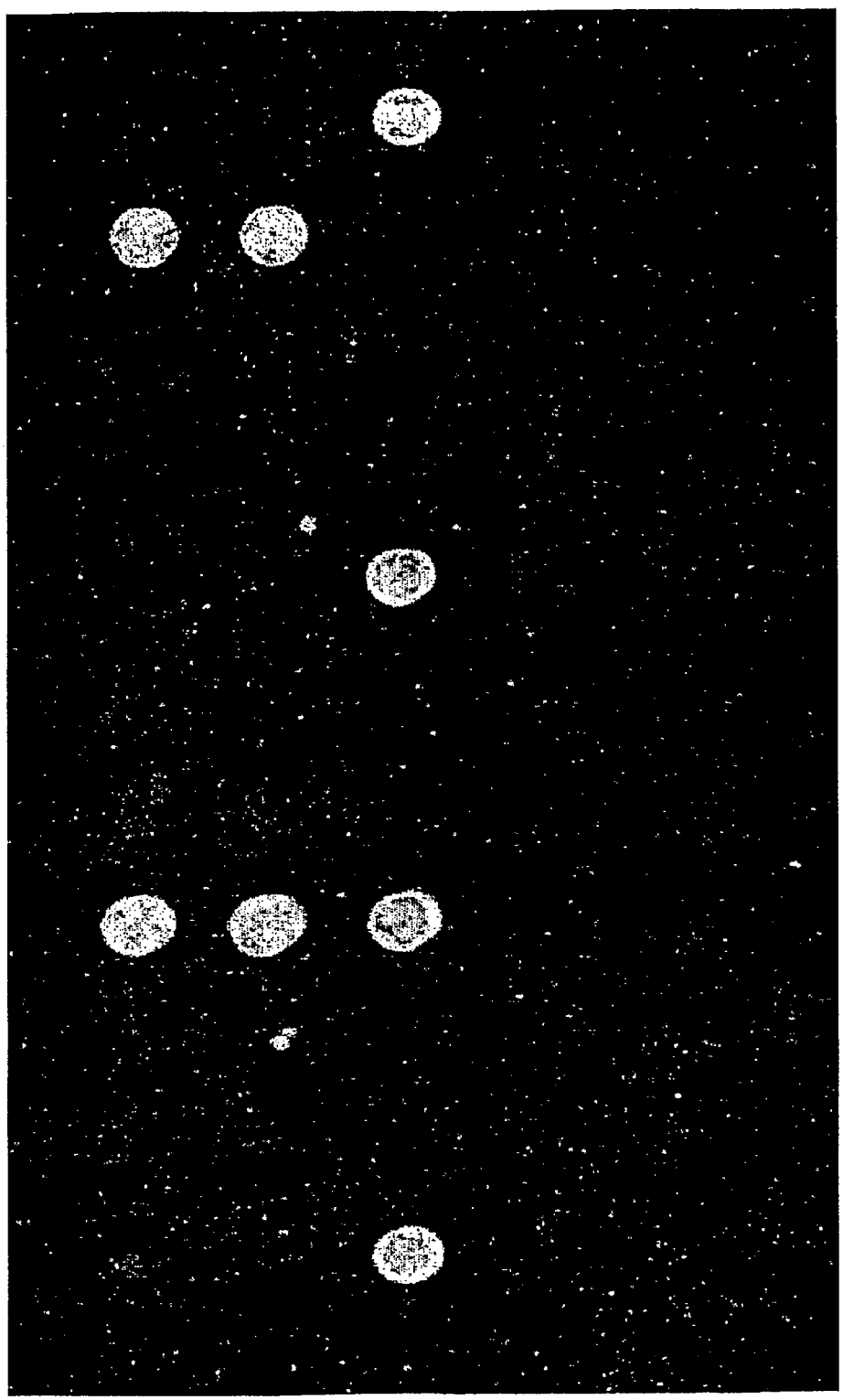
FIG. 3h is a photograph showing the result of analyzing a sample double-infected with HPV 33 and HPV 56 using the DNA chip of the present invention.
Figure 31:
Figure 3J:
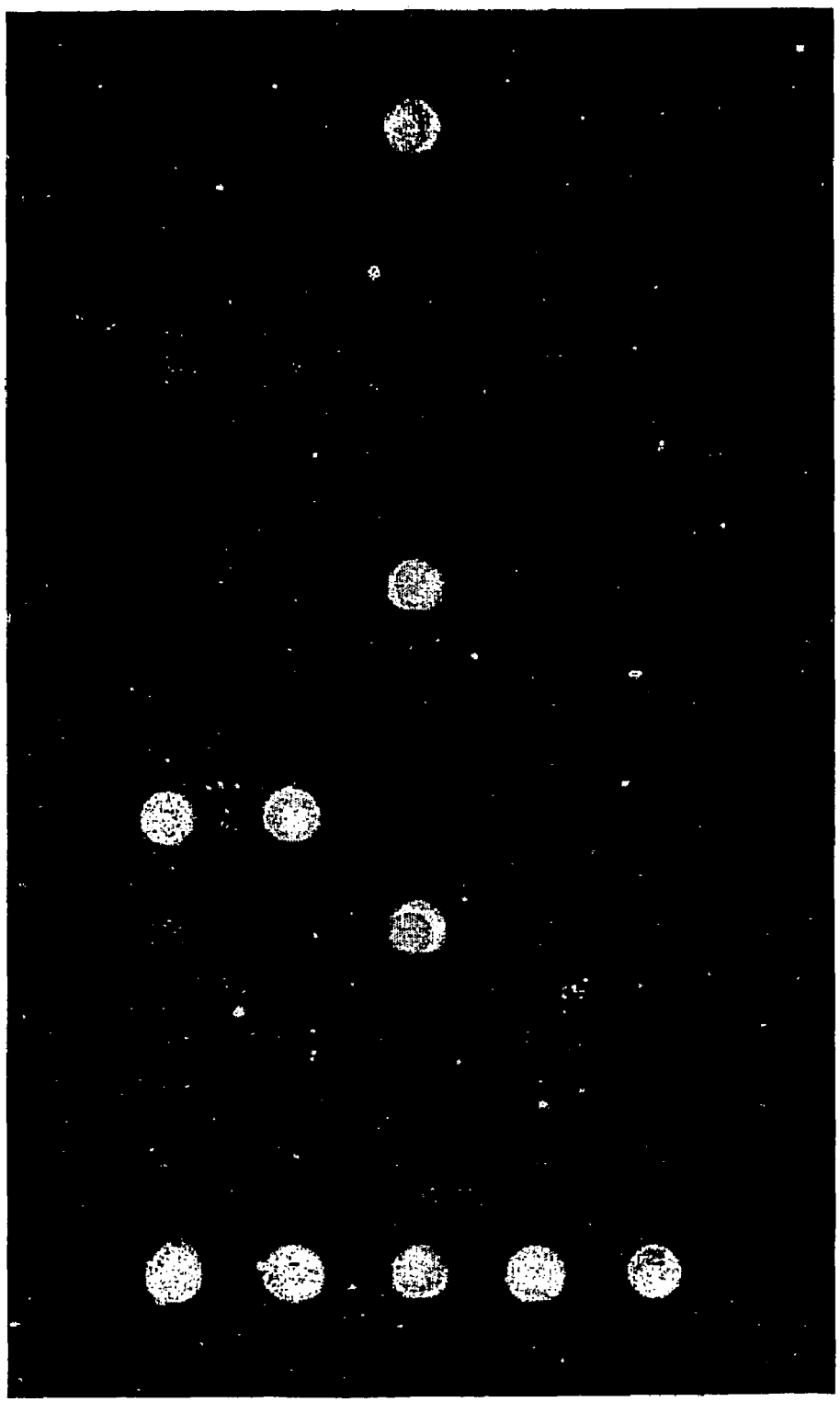
FIG. 3j is a photograph showing the result of analyzing a sample triple-infected with HPV 16, HPV 35 and HPV 59 using the DNA chip of the present invention.

FIG. 1 is a schematic representation of the type and position of the probes on the DNA chip: each number indicates each HPV probe, circles(○) indicate HPV and beta-globin probe-affixed positions, and closed circles(●) indicate background markers to verify proper performance of the hybridization reaction and position markers for locating probes. FIGS. 2a-2e are photographs showing the results of high-risk group HPV DNA analyses using HPV plasmids and cervical cancer cell lines (HPV 16, 18, 39, 58 and 69), and FIGS. 2g-2i are photographs showing the results of low-risk group HPV DNA analyses using HPV plasmids (HPV 6, 11 and 40). As shown in FIGS. 2a-2e and FIGS. 2g-2i, hybridization signals produced by the amplified DNA of HPV plasmid standards and HPV positive controls (cervical cancer cell lines) were observed clearly on the corresponding probes without significant cross-hybridization.

EXAMPLE 6

Detection of HPV Infection in Clinical Samples Using DNA Chip

In order to examine the accuracy and efficiency of diagnosis by the DNA chip of the invention, clinical samples were PCR amplified with primers comprising nucleotide sequences set forth in SEQ ID NO: 43-46, and then, for proper samples, a diagnostic procedure using the DNA chip was performed to detect HPV infection as well as to determine the type of infection.

DNA isolated from 213 uterine cervix specimens were amplified using the method described in Example 4-3, and analyzed for HPV infection by using the DNA chip of the invention. Detection of HPV included in the high-risk group was carried out using a Hybrid Capture II method provided by the Digene Diagnostics company. The results of the two methods were compared (see: FIGS. 2a-2l, FIGS. 3a-3j, and Table 3). FIGS. 2a-2l and FIGS. 3a-3j are photographs showing Examples of the results of DNA chip analyses of cervical swab specimens for HPV infection. As shown in the Figures, detailed diagnoses of HPV infection in the clinical samples via accurate detection and genotyping of the infecting HPV were successfully accomplished by using the DNA chip of the invention. The results of the DNA chip analyses and Hybrid Capture II analysis are shown in Table 3:

TABLE 3

DNA Chip of the Present Invention

| Hybrid Capture II | Group | HPV Type | The Number of Single-infected Samples (The Number of Whole Infected samples) | Percent (%) |
|---|---|---|---|---|
| Positive 149 | High-risk Group | HPV 16 | 31 *1(66) | 20.8 (44.3) |
| | | HPV 18 | 1 (18) | 0.7 (12.1) |
| | | HPV 31 | 2 (3) | 1.4 (2) |
| | | HPV 33 | 2 (6) | 1.4 (4) |
| | | HPV 35 | 2 (6) | 1.4 (4) |
| | | HPV 39 | 1 (3) | 0.7 (2) |
| | | HPV 45 | — (1) | — (0.7) |
| | | HPV 51 | 6 (9) | 4 (6) |
| | | HPV 52 | 10 (14) | 6.7 (9.4) |
| | | HPV 56 | 15 (27) | 10.1 (18.1) |
| | | HPV 58 | 7 (13) | 4.7 (8.7) |
| | | HPV 59 | 2 (7) | 1.4 (4.7) |
| | | HPV 66 | 1 | 0.7 |
| | | HPV 68 | 2 (6) | 1.4 (4) |
| | | HPV 69 | — | — |
| | Low-risk Group | HPV 6 | — (1) | — (0.7) |
| | | HPV 11 | 1 (2) | 0.7 (1.4) |
| | | HPV 34 | 1 (2) | 0.7 (1.4) |
| | | HPV 40 | 1 (2) | 0.7 (1.4) |
| | | HPV 42 | — | |
| | | HPV 43 | 1 | 0.7 |
| | | HPV 44 | — (1) | — (0.7) |
| | Other type | | 4 | 2.7 |
| Negative 51 | Negative 50 | HPV 18 | 1 | |

*1( ): the number of samples compromising multiple-infected samples
In Table 1, "—" indicates absence of sample infected with HPV in the corresponding item, and percent was calculated by {(the number of single-infected samples or total number of infected samples)/149} × 100.

*1( ): the number of samples comprising multiple-infected samples

In Table 1, "–" indicates absence of sample infected with HPV in the corresponding item, and percent was calculated by {(the number of single-infected samples or total number of infected samples)/149}×100.

TABLE 4

Specificity and Sensitivity of DNA chip according to the invention

| DNA Chip Of The Invention | Hybrid Capture II | | |
|---|---|---|---|
| | Positive | Negative | Sum |
| Positive | 162 | 1* | 163 |
| Negative | 0 | 50 | 50 |
| Sum | 162 | 51 | 213 |
| Relative Sensitivity | 100% | | |
| Relative Specificity | 98% (95% Cl = 94-100) | | |
| Similarity | 98.6% (95% Cl = 99-100) | | |
| Copy Value(κ) | 0.99 (95% Cl = 0.96-1.00) | | |

As shown in Table 4, DNA chip analysis according to the invention was reported to have 100% relative sensitivity and 98% relative specificity as compared with the Hybrid Capture assay. The above information indicates that diagnosis of HPV infection using the genotyping kit of the invention is superior in many aspects to the conventional methods employed for the same purpose.

In Tables 3 and 4, all samples which were confirmed as positive by Hybrid Capture assay were tested or diagnosed with the DNA chip of the invention, and one of samples which were confirmed as positive by Hybrid Capture assay was detected to be HPV 18 type. As a result of sequencing to determine whether it was a false-positive, it was confirmed that it was HPV 18. While the Hybrid Capture assay can only diagnosis HPV infection, the DNA chip analysis can detect HPV infection and identify the types of infecting HPV in a fast and accurate manner. The DNA chip analysis according to the invention is so highly sensitive that it can detect the samples confirmed to be false-negative through the Hybrid Capture assay. As well-known to those skilled in the art, HIV16 type shows the highest frequency in HIV infection, followed by HIV 56, 58 and 52 types in contrast to the Western tendency with HPV 18 being the second frequent type.

As clearly illustrated and demonstrated above, the present invention provides a genotyping kit comprising said probes (SEQ ID NO: 1 to 30) for identifying genotypes of HPV from clinical samples of infected patients and a method for diagnosis of HPV infection by genotyping the infecting virus using the said genotyping kit.

Comparative Example 1

As shown in Table 6, efficiency of the probes according to the invention was compared with that of the conventional probes for HPV 16, 34, 56, and 59, and a DNA chip to confirm efficiencies of additional probes for HPV 43, 68, and 69 was described. A test was carried out analogously as in Example 6, except for employing the DNA chip described above.

Figure 8:
FIG. 8 is a photograph showing the result of HPV 66 DNA analysis using the HPV 66 probes of the present invention and the HPV 66 probes of the prior art.

As a result of analysis of control DNA for each type in FIGS. 7-8, conventional probes were found to pose non-specificity (false positive) and low-sensitivity (false negative).

Comparative Example 2

DNA Chip Test

A test was carried out analogously as in Example 6, except for employing the conventional probes including probes set forth in SEQ ID NO: 31-41 and 47-54 and using the DNA chip of the invention. Sequencing was performed using the conventional sequencing method.

Results of analysis using the conventional DNA chip art and the present DNA chip, results of sequencing via PCR for identification, and results of analysis using the conventional probes and the present probes are shown in Tables 5a and 5b. It was found that in the frequency of false negative and false positive, the genotyping kit using the conventional DNA chip is higher than the genotyping kit using the DNA chip of the invention.

The present invention provides a genotyping kit for diagnosing patients infected with human papillomavirus (HPV), which includes the said probes, and a method for genotyping of HPV DNA isolated from patients using the said genotyping kit in an accurate and fast manner.

TABLE 5A

| Sample | Conventional HPV DNA Chip | DNA Chip Of The Invention | Sequencing | Conventional HPV DNA Chip False Positive | Conventional HPV DNA Chip False Negative |
|---|---|---|---|---|---|
| 1 | OT | 16, 68 | 16, 68 | | 16, 68 |
| 2 | 35 | 51 | 51 | 35 | 51 |
| 3 | 16 | OT | OT | 16 | |
| 4 | 59 | 59, 68 | 59, 68 | | 68 |
| 5 | 40, 58 | 51 | 51 | 40, 58 | 51 |
| 6 | 16, 18, 33, 35 | 16, 18, 33 | 16, 18, 33 | 35 | |
| 7 | 33 | 16, 33 | 16, 33 | | 16 |
| 8 | 16 | 16, 68 | 16, 68 | | 68 |
| 9 | 58 | 16, 18 | 16, 18 | 58 | 16, 18 |
| 10 | 16 | 56 | 56 | 16 | 56 |
| 11 | 16 | 56, 58 | 56, 58 | 16 | 56, 58 |
| 12 | 16 | 56 | 56 | 16 | 56 |
| 13 | 35 | 68 | 68 | 35 | |
| 14 | 16 | 16, 69 | 16, 69 | | 69 |
| 15 | 35, 52 | 52 | 52 | 35 | 52 |
| 16 | 16 | 18, 56 | 18, 56 | 16 | 18, 52 |
| 17 | 35 | 52 | 52 | 35 | 52 |
| 18 | 35 | 51 | 51 | 35 | 51 |
| 19 | 58 | 40 | 40 | 58 | 40 |
| 20 | 59 | 52 | 52 | 59 | 52 |
| 21 | 59 | 16 | 16 | 59 | 16 |
| 22 | 35 | 16, 18 | 16, 18 | 35 | 16, 18 |
| 23 | 35 | 16, 18 | 16, 18 | 35 | 16, 18 |
| 24 | 35 | 43 | 43 | 35 | 43 |
| 25 | 16 | 52 | 52 | 16 | 52 |
| 26 | 35, 16 | 35 | 35 | 16 | |
| 27 | 58 | 31, 39, 58 | 31, 39, 58 | | 31, 39 |
| 28 | 31, 59 | 31 | 31 | 59 | 31 |
| 29 | 31, 16 | 31 | 31 | 16, 35 | 31 |
| 30 | 35, 16 | 31 | 31 | 16, 35 | 31 |
| 31 | 35, 58 | 35, 58 | 35, 58 | | |
| 32 | 35, 33 | 33 | 33 | 35 | 33 |

TABLE 5B

| | | | | | |
|---|---|---|---|---|---|
| 33 | 16, 35 | 16 | 16 | 35 | |
| 34 | 52, 40 | 52, 66 | 52, 66 | 40 | 66 |
| 35 | 58 | 66, 58 | 66, 58 | | 66 |
| 36 | 16, 56 | 16 | 16 | 56 | |
| 37 | 58, 34 | 58 | 58 | 34 | |
| 38 | 16 | 16, 43 | 16, 43 | | 43 |
| 39 | 31, 35 | 31 | 31 | 35 | |
| 40 | 33, 16 | 33 | 33 | 16 | |
| 41 | 16 | 18 | 18 | 16 | |
| 42 | 16, 40 | neg | neg | 16, 40 | |
| 43 | 16, 56 | neg | neg | 16, 56 | |
| 44 | 16, 59 | 16 | 16 | 59 | |
| 45 | 35 | 35, 66 | 35, 66 | | 66 |
| 46 | 16, 40 | 16 | 16 | 40 | |
| 47 | 34, 58 | 58 | 58 | 34 | |
| 48 | 6, 18 | 6, 18, 69 | 6, 18, 69 | | 69 |
| 49 | 58 | 51 | 51 | 58 | 51 |
| 50 | 59 | 11 | 11 | 59 | 11 |

The HPV genotyping kit of the invention is an implement that can detect HPV infection in a simple and accurate manner, as well as identify the types of infecting HPV, and therefore it may contribute to early diagnosis, prevention, and treatment of cervical cancer.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A DNA chip for genotyping HPV comprising a plurality of HPV probes, wherein the plurality of HPV probes comprises each of the nucleotide sequences listed in SEQ ID NOS: 1-41, or the complement thereof, and wherein each probe in the plurality of HPV probes consists of one of the nucleotide sequences listed in SEQ ID NOS: 1-41, or the complement thereof.

2. An HPV genotyping kit which comprises:
(i) a DNA chip for genotyping HPV according to claim 1;
(ii) primers for amplifying sample DNA by PCR, wherein the primers are SEQ ID NOS: 43 and 44; and
(iii) labels for labeling DNA that is amplified and hybridized to said DNA chip, wherein the labels are selected from the group consisting of Cy5, Cy3, biotin-binding material, EDANS (5-(2'-aminoethyl)amino-1-naphthalene sulfuric acid), tetramethylrhodamine (TMR), tetramethylrhodamine isocyanate (TMRITC), x-rhodamine, and Texas red.

3. The HPV genotyping kit according to claim 2, wherein the DNA chip further comprises position markers to locate probes.

4. The HPV genotyping kit according to claim 3, wherein the position markers are selected from the group consisting of β-globin, actin, and glyceraldehyde-3-phosphate dehydrogenase gene.

5. The HPV genotyping kit according to claim 2, further comprising primers for amplifying β-globin wherein the primers are SEQ ID NO: 45 and 46.

* * * * *